United States Patent [19]
Biftu et al.

[11] Patent Number: 6,034,106
[45] Date of Patent: Mar. 7, 2000

[54] OXADIAZOLE BENZENESULFONAMIDES AS SELECTIVE $\beta_3$ AGONIST FOR THE TREATMENT OF DIABETES AND OBESITY

[75] Inventors: Tesfaye Biftu, Westfield; Michael H. Fisher, Ringoes; Danqing Dennis Feng, Branchburg; Chan-Hwa Kuo, South Plainfield; Gui-Bai Liang, Scotch Plains; Elizabeth M. Naylor, Scotch Plains; Ann E. Weber, Scotch Plains, all of N.J.

[73] Assignee: Merck & Co., Inc., Rahway, N.J.

[21] Appl. No.: 08/868,556

[22] Filed: Jun. 4, 1997

Related U.S. Application Data

[60] Provisional application No. 60/019,295, Jun. 7, 1996.

[51] Int. Cl.$^7$ .......................... C07D 413/10; A61K 31/44
[52] U.S. Cl. ....................... 514/340; 546/269.1; 546/330; 514/357
[58] Field of Search .................................... 514/340, 357; 546/269.1, 330

[56] References Cited

U.S. PATENT DOCUMENTS 5,561,142 10/1996 Fisher et al. .............................. 514/312

*Primary Examiner*—Jane Fan
*Attorney, Agent, or Firm*—Mollie M. Yang; David L. Rose

[57] ABSTRACT

Oxadiazole substituted benzenesulfonamides are selective $\beta_3$ adrenergic receptor agonists with very little $\beta_1$ and $\beta_2$ adrenergic receptor activity and as such the compounds are capable of increasing lipolysis and energy expenditure in cells. The compounds thus have potent activity in the treatment of Type II diabetes and obesity. The compounds can also be used to lower triglyceride levels and cholesterol levels or raise high density lipoprotein levels or to decrease gut motility. In addition, the compounds can be used to reduced neurogenic inflammation or as antidepressant agents. The compounds are prepared by coupling an aminoalkylphenyl-sulfonamide with an appropriately substituted epoxide. Compositions and methods for the use of the compounds in the treatment of diabetes and obesity and for lowering triglyceride levels and cholesterol levels or raising high density lipoprotein levels or for increasing gut motility are also disclosed.

4 Claims, No Drawings

OXADIAZOLE BENZENESULFONAMIDES AS SELECTIVE β₃ AGONIST FOR THE TREATMENT OF DIABETES AND OBESITY

CROSS REFERENCE TO RELATED APPLICATIONS

This application is based on, and claims priority from, provisional application 60/019,295 filed on Jun. 7, 1996.

BACKGROUND OF THE INVENTION

β-Adrenoceptors have been subclassified as $\beta_1$ and $\beta_2$ since 1967. Increased heart rate is the primary consequence of $\beta_1$-receptor stimulation, while bronchodilation and smooth muscle relaxation typically result from $\beta_2$ stimulation. Adipocyte lipolysis was initially thought to be solely a $\beta_1$-mediated process. However, more recent results indicate that the receptor-mediating lipolysis is atypical in nature. These atypical receptors, later called $\beta_3$-adrenoceptors, are found on the cell surface of both white and brown adipocytes where their stimulation promotes both lipolysis (breakdown of fat) and energy expenditure.

Early developments in this area produced compounds with greater agonist activity for the stimulation of lipolysis ($\beta_3$ activity) than for stimulation of atrial rate ($\beta_1$) and tracheal relaxation ($\beta_2$). These early developments disclosed in Ainsworth et al., U.S. Pat. Nos. 4,478,849 and 4,396,627, were derivatives of phenylethanolamines.

Such selectivity for $\beta_3$-adrenoceptors could make compounds of this type potentially useful as antiobesity agents. In addition, these compounds have been reported to show antihyperglycemic effects in animal models of non-insulin-dependent diabetes mellitus.

A major drawback in treatment of chronic diseases with $\beta_3$ agonists is the potential for stimulation of other β-receptors and subsequent side effects. The most likely of these include muscle tremor ($\beta_2$) and increased heart rate ($\beta_1$). Although these phenylethanolamine derivatives do possess some $\beta_3$ selectivity, side effects of this type have been observed in human volunteers. It is reasonable to expect that these side effects resulted from partial $\beta_1$ and/or $\beta_2$ agonism.

More recent developments in this area are disclosed in Ainsworth et al., U.S. Pat. No. 5,153,210, Caulkett et al., U.S. Pat. No. 4,999,377, Alig et al., U.S. Pat. No. 5,017,619, Lecount et al., European Patent 427480 and Bloom et al., European Patent 455006.

Even though these more recent developments purport to describe compounds with greater $\beta_3$ selectivity over the $\beta_1$ and $\beta_2$ activities, this selectivity was determined using rodents, in particular, rats as the test animal. Because even the most highly selective compounds, as determined by these assays, still show signs of side effects due to residual $\beta_1$ and $\beta_2$ agonist activity when the compounds are tested in humans, it has become apparent that the rodent is not a good model for predicting human $\beta_3$ selectivity.

Recently, assays have been developed which more accurately predict the effects that can be expected in humans. These assays utilize cloned human $\beta_3$ receptors which have been expressed in Chinese hamster ovary cells. See Emorine et al, *Science*, 1989, 245:1118–1121; and Liggett, *Mol. Pharmacol.*, 1992, 42:634–637. The agonist and antagonist effects of the various compounds on the cultivated cells provide an indication of the antiobesity and antidiabetic effects of the compounds in humans.

U.S. Pat. No. 5,451,677 discloses selective β3 agonists of the formula:

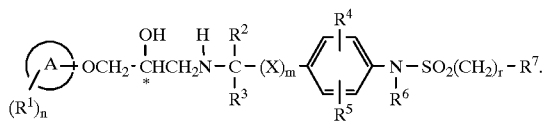

PCT Application WO95/29159 published Nov. 2, 1995 (U.S. Pat. No. 5,561,142) discloses selective β3 agonists of the formula

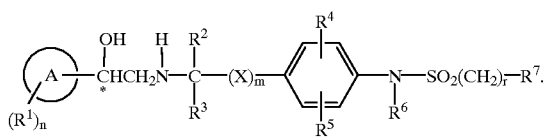

Compounds of the present invention represent a novel selection within the disclosure of WO95/29159.

SUMMARY OF THE INVENTION

The instant invention is concerned with oxadiazole substituted benzenesulfonamides which are useful as antiobesity and antidiabetic compounds. Thus, it is an object of this invention to describe such compounds. It is a further object to describe the specific preferred stereoisomers of the substituted sulfonamides. A still further object is to describe processes for the preparation of such compounds. Another object is to describe methods and compositions which use the compounds as the active ingredient thereof. Further objects will become apparent from reading the following description.

DESCRIPTION OF THE INVENTION

The present invention provides compounds having the formula I:

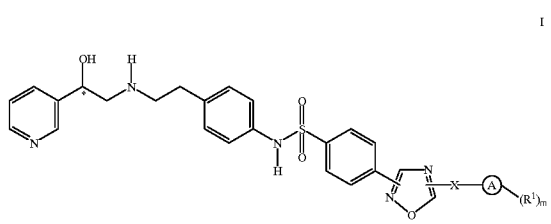

wherein
X is
 (1) a bond,
 (2) $C_1$–$C_3$ alkylene optionally substituted with 1 or 2 groups selected from methyl, $C_1$–$C_5$ alkoxy, hydroxy, and halogen,
 (3) $C_1$–$C_3$ alkylene optionally substituted with 1 or 2 groups selected from methyl, $C_1$–$C_5$ alkoxy, hydroxy, and halogen, wherein said alkylene contains up to two groups selected from Q and carbonyl,
 (4) carbonyl, or
 (5) Q;
m is 0 to 5;

A is
(1) phenyl,
(2) a 5 or 6-membered heterocyclic ring with from 1 to 4 heteroatoms selected from oxygen, sulfur and nitrogen,
(3) a benzene ring fused to a $C_5$–$C_{10}$ carbocyclic ring,
(4) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen, or
(5) a 5 or 6-membered heterocyclic ring with from 1 to 4 heteroatoms selected from oxygen, sulfur and nitrogen fused to a $C_5$–$C_{10}$ carbocyclic ring;

$R^1$ is
(1) $C_1$–$C_{10}$ alkyl optionally substituted with up to 5 groups selected from
  (a) hydroxy,
  (b) halogen,
  (c) cyano,
  (d) $QR^2$,
  (e) $C_3$–$C_8$ cycloalkyl,
  (f) A optionally substituted with up to 5 groups selected from halogen, $C_1$–$C_{10}$ alkyl and $C_1$–$C_{10}$ alkoxy,
  (g) $Q'COR^3$,
  (h) $S(O)_n R^3$, where n is 0 to 2,
  (i) $NR^2SO_2R^3$,
  (j) $NR^2CO_2R^2$, and
  (k) $CO_2R^2$,
(2) $C_3$–$C_8$ cycloalkyl,
(3) oxo,
(4) halogen,
(5) cyano,
(6) $QR^2$,
(7) $S(O)_n R^3$, where n is 0 to 2,
(8) $Q'COR^3$,
(9) $NR^2SO_2R^3$,
(10) $NR^2CO_2R^2$,
(11) A optionally substituted with up to 5 groups independently selected from
  (a) $R^2$,
  (b) $QR^2$,
  (c) halogen, and
  (d) oxo; or
(12) $CO_2R^2$;

$R^2$ is
(1) hydrogen,
(2) $C_1$–$C_{10}$ alkyl optionally substituted with up to 5 groups selected from
  (a) hydroxy,
  (b) halogen,
  (c) $CO_2R^4$,
  (d) $S(O)_n$—C1–C10 alkyl, where n is 0 to 2,
  (e) $C_3$–$C_8$ cycloalkyl,
  (f) $C_1$–$C_{10}$ alkoxy, and
  (g) A optionally substituted with up to 5 groups selected from halogen, $C_1$–$C_{10}$ alkyl and $C_1$–$C_{10}$ alkoxy,
(3) $C_3$–$C_8$ cycloalkyl, or
(4) A optionally substituted with up to 5 groups selected from
  (a) halogen,
  (b) nitro,
  (c) oxo,
  (d) $NR^4R^4$,
  (e) $C_1$–$C_{10}$ alkoxy,
  (f) $S(O)_n$—$C_1$–$C_{10}$ alkyl, where n is 0 to 2, and
  (g) $C_1$–$C_{10}$ alkyl optionally substituted with up to 5 groups selected from hydroxy, halogen, $CO_2R^4$, $S(O)_n$—$C_1$–$C_{10}$ alkyl, where n is 0 to 2, $C_3$–$C_8$ cycloalkyl, $C_1$–$C_{10}$ alkoxy, and A optionally substituted with up to 5 groups selected from halogen, $C_1$–$C_{10}$ alkyl and $C_1$–$C_{10}$ alkoxy;

$R^3$ is
(1) $R^2$ or
(2) $NR^2R^2$;

$R^4$ is
(1) H, or
(2) $C_1$–$C_{10}$ alkyl;

Q is
(1) $N(R^2)$,
(2) O or
(3) $S(O)_n$, and n is 0 to 2;

Q" is
(1) $N(R^2)$,
(2) O or
(3) a bond; or a pharmaceutically acceptable salt thereof.

Compounds of the present invention are a novel selection within the generic structure disclosed in WO95/29159. The present compounds are potent and selective β3 agonists, and have improved oral bioavailability in animals.

In one subset of compounds of formula IX is $C_1$–$C_3$ alkylene, optionally substituted with one or two groups selected from methyl, and halogen. In one embodiment X is —$CH_2$—, $CH(CH_3)$—, —$C(CH_3)_2$ or —CH(F)—, and a preferred embodiment is where X is —$CH_2$—.

In another subset X is $C_1$–$C_3$ alkylene-O, $C_1$–$C_3$ alkylene-carbonyl or N(R2), wherein the alkylene is optionally substituted with one or two groups selected from methyl, and halogen. In one embodiment X is —$CH_2O$— or —$C(CH_3)_2O$—, wherein the point of attachment to the oxadiazole ring is the carbon atom and the point of attachment to the A group is the oxygen atom; and a preferred embodiment is where X is $CH_2O$.

The oxadiazole ring may be attached to the benzenesulfonamide moiety via either the C3 carbon or the C5 carbon atom. The numbering of the oxadiazole ring is as shown below:

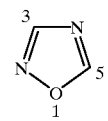

Accordingly, compounds of formulae Ia and Ib are provided:

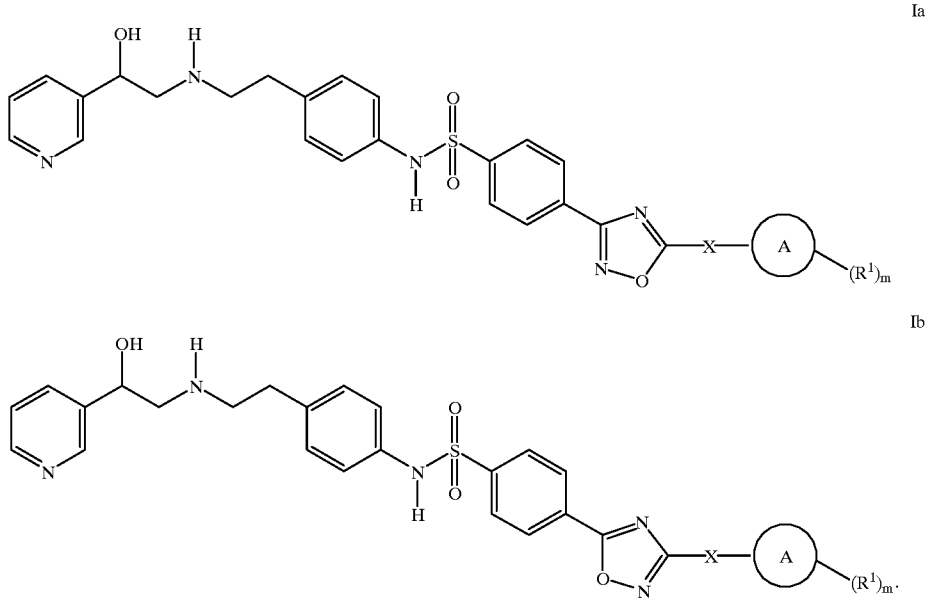

Another subset of compounds of formula I provides compounds wherein A is (1) phenyl, (2) naphthyl, (3) a 5 or 6-membered heterocyclic ring with from 1 to 4 heteroatoms selected from oxygen, sulfur and nitrogen, or (4) a benzene ring fused to a 5 or 6-membered heterocyclic ring with from 1 to 4 heteroatoms selected from oxygen, sulfur and nitrogen.

Another subset of compounds of formnula I provides compounds where $R^1$ is (1) $C_1$–$C_{10}$ alkyl optionally substituted with up to 5 groups selected from hydroxy, halogen, cyano, $QR^2$, $C_3$–$C_8$ cycloalkyl, A optionally substituted with up to 5 groups selected from halogen, $C_1$–$C_{10}$ alkyl and $C_1$–$C_{10}$ alkoxy, $Q'COR^3$, $S(O)_nR^3$ where n is 0 to 2, $NR^2SO_2R^3$, and $NR^2CO_2R^2$, (2) halogen, (3) $QR^2$, (4) $S(O)_nR^3$ where n is 0 to 2, (5) $Q'COR^3$, (6) phenyl optionally substituted with up to 4 groups independently selected from $R^2$, $QR^2$ and halogen, or (7) 5 or 6-membered heterocycle with from 1 to 4 heteroatoms selected from oxygen, sulfur and nitrogen, optionally substituted with up to 4 groups independently selected from oxo, $R^2$, $QR^2$ and halogen.

In a preferred embodiment of compounds of formula I, X is $CH_2$ or $CH_2O$ in which O is attached to A; A is (1) phenyl, (2) naphthyl, (3) a 5 or 6-membered heterocyclic ring with from 1 to 4 heteroatoms selected from oxygen, sulfur and nitrogen, or (4) a benzene ring fused to a 5 or 6-membered heterocyclic ring with from 1 to 4 heteroatoms selected from oxygen, sulfur and nitrogen; $R^1$ is (1) $C_1$–$C_{10}$ alkyl optionally substituted with up to 5 groups selected from halogen, cyano, $QR^2$, and A optionally substituted with up to 5 groups selected from halogen, $C_1$–$C_{10}$ alkyl and $C_1$–$C_{10}$ alkoxy, (2) halogen, (3) phenyl optionally substituted with up to 5 groups independently selected from $R^2$, $QR^2$ and halogen, (4) 5 or 6-membered heterocycle with from 1 to 4 heteroatoms selected from oxygen, sulfur and nitrogen, optionally substituted with up to 4 groups independently selected from $R^2$, $QR^2$ and halogen, or (5) $QR^2$; $R^2$ is (1) $C_1$–$C_{10}$ alkyl optionally substituted with up to 5 groups selected from halogen, $C_1$–$C_{10}$ alkoxy, and A optionally substituted with up to 5 groups selected from halogen, $C_1$–$C_{10}$ alkyl and $C_1$–$C_{10}$ alkoxy, (2) A optionally substituted with up to 5 groups selected from halogen, $NR^4R^4$, $C_1$–$C_{10}$ alkoxy, $C_1$–$C_{10}$ alkylthio, and $C_1$–$C_{10}$ alkyl optionally substituted with up to 5 groups selected from halogen, $C_3$–$C_8$ cycloalkyl, $C_1$–$C_{10}$ alkoxy, and A optionally substituted with up to 5 groups selected from halogen, $C_1$–$C_{10}$ alkyl and $C_1$–$C_{10}$ alkoxy; Q is $N(R^2)$, O or S.

In a more preferred embodiment, X is $CH_2$ or $CH_2O$ in which O is attached to A; A is (1) phenyl, (2) naphthyl, (3) a 5 or 6-membered heterocyclic ring with from 1 to 4 heteroatoms selected from oxygen, sulfur and nitrogen, or (4) a benzene ring fused to a 5 or 6-membered heterocyclic ring with from 1 to 4 heteroatoms selected from oxygen, sulfur and nitrogen; $R^1$ is (1) $C_1$–$C_{10}$ alkyl optionally substituted with up to 5 groups selected from halogen, and A optionally substituted with up to 5 groups selected from halogen, $C_1$–$C_{10}$ alkyl and $C_1$–$C_{10}$ alkoxy, (2) halogen, (3) 5 or 6-membered heterocycle with from 1 to 4 heteroatoms selected from oxygen, sulfur and nitrogen, optionally substituted with up to 4 groups selected from halogen, $C_1$–$C_{10}$ alkyl and $C_1$–$C_{10}$ alkoxy, or (4) $QR^2$; $R^2$ is $C_1$–$C_{10}$ alkyl, optionally substituted with up to 5 halogen atoms; and Q is O.

Representative antiobesity and antidiabetic compounds of the present invention include the following:

N-[4-[2-[[2-hydroxy-2-(3-pyridinyl)ethyl]amino]ethyl]phenyl]-4-[5-(5-methylisoxazol-3-yl)-[1,2,4]-oxadiazol-3-yl]benzensulfonamide, N-[4-[2-[[2-hydroxy-2-(3-pyridinyl)ethyl]amino]ethyl]phenyl]-4-[5-(4-fluorophenyl)-[1,2,4]-oxadiazol-3-yl]benzensulfonamide, N-[4-[2-[[2-hydroxy-2-(3-pyridinyl)ethyl]amino]ethyl]phenyl]-4-[5-(3-fluorophenyl)-[1,2,4]-oxadiazol-3-yl]benzensulfonamide, N-[4-[2-[[2-hydroxy-2-(3-pyridinyl)ethyl]amino]ethyl]phenyl]-4-[5-(2,5-difluorophenyl)-[1,2,4]-oxadiazol-3-yl]benzensulfonamide, N-[4-[2-[[2-hydroxy-2-(3-pyridinyl)ethyl]amino]ethyl]phenyl]-4-[5-(3,5-difluorophenyl)-[1,2,4]-oxadiazol-3-yl]benzensulfonamide, N-[4-[2-[[2-hydroxy-2-(3-pyridinyl)ethyl]amino]ethyl]phenyl]-4-[5-(3-trifluoromethylphenyl)-[1,2,4]-oxadiazol-3-yl]benzensulfonamide, N-[4-[2-[[2-hydroxy-2-(3-pyridinyl)ethyl]amino]ethyl]
phenyl]-4-[5-(3-nitrophenyl)-[1,2,4]-oxadiazol-3-yl]
benzensulfonanide, N-[4-[2-[[2-hydroxy-2-(3-pyridinyl)ethyl]amino]ethyl]
phenyl]-4-[5-(3-methylthiophenyl)-[1,2,4]-oxadiazol-3-
yl]benzensulfonamide, N-[4-[2-[[2-hydroxy-2-(3-pyridinyl)ethyl]amino]ethyl]
phenyl]-4-[5-(3-methylsulfonylphenyl)-[1,2,4]-
oxadiazol-3-yl]benzensulfonamnide, N-[4-[2-[[2-hydroxy-2-(3-pyridinyl)ethyl]amino]ethyl]
phenyl]-4-[5-(2-methylphenyl)-[1,2,4]-oxadiazol-3-yl]
benzensulfonamide, N-[4-[2-[[2-hydroxy-2-(3-pyridinyl)ethyl]amino]ethyl]
phenyl]-4-[5-(3-methylphenyl)-[1,2,4]-oxadiazol-3-yl]
benzensulfonamide, N-[4-[2-[[2-hydroxy-2-(3-pyridinyl)ethyl]amino]ethyl]
phenyl]-4-[5-(3-methoxyphenyl)-[1,2,4]-oxadiazol-3-yl]
benzensulfonamide, N-[4-[2-[[2-hydroxy-2-(3-pyridinyl)ethyl]amino]ethyl]
phenyl]-4-[5-(3-pyridyl)-[1,2,4]-oxadiazol-3-yl]
benzensulfonamide, N-[4-[2-[[2-hydroxy-2-(3-pyridinyl)ethyl]amino]ethyl]
phenyl]-4-[5-(2,3-dimethoxyphenyl)-[1,2,4]-oxadiazol-
3-yl]benzensulfonamnide, N-[4-[2-[[2-hydroxy-2-(3-pyridinyl)ethyl]amino]ethyl]
phenyl]-4-[5-(2-benzofuranyl)-[1,2,4]-oxadiazol-3-yl]
benzensulfonamide, N-[4-[2-[[2-hydroxy-2-(3-pyridinyl)ethyl]amino]ethyl]
phenyl]-4-[5-(5-fluoro-2-indolyl)-[1,2,4]-oxadiazol-3-yl]
benzensulfonamide, N-[4-[2-[[2-hydroxy-2-(3-pyridinyl)ethyl]amino]ethyl]
phenyl]-4-[5-[2-(4-fluorophenyl)ethyl]-[1,2,4]-
oxadiazol-3-yl]benzensulfonamide, N-[4-[2-[[2-hydroxy-2-(3-pyridinyl)ethyl]amino]ethyl]
phenyl]-4-[5-[2-(3,4-difluorophenyl)ethyl]-[1,2,4]-
oxadiazol-3-yl]benzensulfonamide, N-[4-[2-[[2-hydroxy-2-(3-pyridinyl)ethyl]amino]ethyl]
phenyl]-4-[5-[2-(4-methoxyphenyl)ethyl]-[1,2,4]-
oxadiazol-3-yl]benzensulfonamide, N-[4-[2-[[2-hydroxy-2-(3-pyridinyl)ethyl]amino]ethyl]
phenyl]-4-[5-[2-(phenyl)ethyl]-[1,2,4]-oxadiazol-3-yl]
benzensulfonamide, N-[4-[2-[[2-hydroxy-2-(3-pyridinyl)ethyl]amino]ethyl]
phenyl]-4-[5-[2-(4-chlorophenyl)ethyl]-[1,2,4]-
oxadiazol-3-yl]benzensulfonamide, N-[4-[2-[[2-hydroxy-2-(3-pyridinyl)ethyl]amino]ethyl]
phenyl]-4-[5-[3-(phenyl)propyl]-[1,2,4]-oxadiazol-3-yl]
benzensulfonamide, N-[4-[2-[[2-hydroxy-2-(3-pyridinyl)ethyl]amino]ethyl]
phenyl]-4-[5-[3-(4-methoxyphenyl)propyl]-[1,2,4]-
oxadiazol-3-yl]benzensulfonamide, N-[4-[2-[[2-hydroxy-2-(3-pyridinyl)ethyl]amino]ethyl]
phenyl]-4-[5-(3-fluorophenylmethyl)-[1,2,4]-oxadiazol-
3-yl]benzensulfonamide, N-[4-[2-[[2-hydroxy-2-(3-pyridinyl)ethyl]amino]ethyl]
phenyl]-4-[5-(4-fluorophenylmethyl)-[1,2,4]-oxadiazol-
3-yl]benzensulfonamide, N-[4-[2-[[2-hydroxy-2-(3-pyridinyl)ethyl]amino]ethyl]
phenyl]-4-[5-(4-chlorophenylmethyl)-[1,2,4]-oxadiazol-
3-yl]benzensulfonamide, N-[4-[2-[[2-hydroxy-2-(3-pyridinyl)ethyl]amino]ethyl]
phenyl]-4-[5-(3,4-difluorophenylmethyl)-[1,2,4]-
oxadiazol-3-yl]benzensulfonamide, N-[4-[2-[[2-hydroxy-2-(3-pyridinyl)ethyl]amino]ethyl]
phenyl]-4-[5-(3,4,5-trifluorophenylmethyl)-[1,2,4]-
oxadiazol-3-yl]benzensulfonamide, N-[4-[2-[[2-hydroxy-2-(3-pyridinyl)ethyl]amino]ethyl]
phenyl]-4-[5-[3,5-bis(trifluoromethyl)phenylmethyl]-[1,
2,4]-oxadiazol-3-yl]benzensulfonamide, N-[4-[2-[[2-hydroxy-2-(3-pyridinyl)ethyl]amino]ethyl]
phenyl]-4-[5-[[4-fluoro-3-(trifluoromethyl)phenyl]
methyl]-[1,2,4]-oxadiazol-3-yl]benzensulfonamide, N-[4-[2-[[2-hydroxy-2-(3-pyridinyl)ethyl]amino]ethyl]
phenyl]-4-[5-[[4-(trifluoromethyl)phenyl]methyl]-[1,2,
4]-oxadiazol-3-yl]benzensulfonamide, N-[4-[2-[[2-hydroxy-2-(3-pyridinyl)ethyl]amino]ethyl]
phenyl]-4-[5-[[4-(methylthio)phenyl]methyl]-[1,2,4]-
oxadiazol-3-yl]benzensulfonamnide, N-[4-[2-[[2-hydroxy-2-(3-pyridinyl)ethyl]amino]ethyl]
phenyl]-4-[5-[[4-(methylsulfonyl)phenyl]methyl]-[1,2,
4]-oxadiazol-3-yl]benzensulfonamide, N-[4-[2-[[2-hydroxy-2-(3-pyridinyl)ethyl]amino]ethyl]
phenyl]-4-[5-(biphen-4-ylmethyl)-[1,2,4]-oxadiazol-3-yl]
benzensulfonamide, N-[4-[2-[[2-hydroxy-2-(3-pyridinyl)ethyl]amino]ethyl]
phenyl]-4-[5-[4-(2-pyridyl)phenylmethyl]-[1,2,4]-
oxadiazol-3-yl]benzensulfonamide, N-[4-[2-[[2-hydroxy-2-(3-pyridinyl)ethyl]amino]ethyl]
phenyl]-4-[5-[4-(3-pyridyl)phenylmethyl]-[1,2,4]-
oxadiazol-3-yl]benzensulfonamide, N-[4-[2-[[2-hydroxy-2-(3-pyridinyl)ethyl]amino]ethyl]
phenyl]-4-[5-[(4-acetamido)phenylmethyl]-[1,2,4]-
oxadiazol-3-yl]benzensulfonamide, N-[4-[2-[[2-hydroxy-2-(3-pyridinyl)ethyl]amino]ethyl]
phenyl]-4-[5-(3-chlorophenylmethyl)-[1,2,4]-oxadiazol-
3-yl]benzensulfonamide, N-[4-[2-[[2-hydroxy-2-(3-pyridinyl)ethyl]amino]ethyl]
phenyl]-4-[5-(2-bromophenylmethyl)-[1,2,4]-oxadiazol-
3-yl]benzensulfonamide, N-[4-[2-[[2-hydroxy-2-(3-pyridinyl)ethyl]amino]ethyl]
phenyl]-4-[5-(4-methylphenylmethyl)-[1,2,4]-oxadiazol-
3-yl]benzensulfonamide, N-[4-[2-[[2-hydroxy-2-(3-pyridinyl)ethyl]amino]ethyl]
phenyl]-4-[5-(2,4-difluorophenylmethyl)-[1,2,4]-
oxadiazol-3-yl]benzensulfonamide, N-[4-[2-[[2-hydroxy-2-(3-pyridinyl)ethyl]amino]ethyl]
phenyl]-4-[5-(3,5-difluorophenylmethyl)-[1,2,4]-
oxadiazol-3-yl]benzensulfonamide, N-[4-[2-[[2-hydroxy-2-(3-pyridinyl)ethyl]amino]ethyl]
phenyl]-4-[5-(3-pyridylmethyl)-[1,2,4]-oxadiazol-3-yl]
benzensulfonamide, N-[4-[2-[[2-hydroxy-2-(3-pyridinyl)ethyl]amino]ethyl]
phenyl]-4-[5-(3-indolylmethyl)-[1,2,4]-oxadiazol-3-yl]
benzensulfonamide, N-[4-[2-[[2-hydroxy-2-(3-pyridinyl)ethyl]amino]ethyl]
phenyl]-4-[5-(2-naphthylmethyl)-[1,2,4]-oxadiazol-3-yl]
benzensulfonamide, N-[4-[2-[[2-hydroxy-2-(3-pyridinyl)ethyl]amino]ethyl]
phenyl]-4-[5-[(5-fluoro-3-indolyl)methyl]-[1,2,4]-
oxadiazol-3-yl]benzensulfonamide, N-[4-[2-[[2-hydroxy-2-(3-pyridinyl)ethyl]amino]ethyl]
phenyl]-4-[5-(3-thienylmethyl)-[1,2,4]-oxadiazol-3-yl]
benzensulfonamide, N-[4-[2-[[2-hydroxy-2-(3-pyridinyl)ethyl]amino]ethyl]
phenyl]-4-[5-[(5-chlorobenzo[b]thien-3-yl)methyl]-[1,2,
4]-oxadiazol-3-yl]benzensulfonamide, N-[4-[2-[[2-hydroxy-2-(3-pyridinyl)ethyl]amino]ethyl]
phenyl]-4-[5-[(benzo[b]thien-3-yl)methyl]-[1,2,4]-
oxadiazol-3-yl]benzensulfonamide, N-[4-[2-[[2-hydroxy-2-(3-pyridinyl)ethyl]amino]ethyl]
phenyl]-4-[5-[(2,3-dihydrobenzofuran-5-yl)methyl]-[1,2,
4]-oxadiazol-3-yl]benzensulfonamide, N-[4-[2-[[2-hydroxy-2-(3-pyridinyl)ethyl]amino]ethyl]
phenyl]-4-[5-(3-oxo-3-(4-fluorophenyl)propyl)-[1,2,4]-
oxadiazol-3-yl]benzensulfonamide, N-[4-[2-[[2-hydroxy-2-(3-pyridinyl)ethyl]amino]ethyl]
phenyl]-4-[5-(2-(naphthyloxy)methyl)-[1,2,4]-oxadiazol-
3-yl]benzensulfonamide, N-[4-[2-[[2-hydroxy-2-(3-pyridinyl)ethyl]amino]ethyl]
    phenyl]-4-[5-(4-fluorophenoxymethyl)-[1,2,4]-
    oxadiazol-3-yl]benzensulfonamide,
N-[4-[2-[[2-hydroxy-2-(3-pyridinyl)ethyl]amino]ethyl]
    phenyl]-4-[5-(3,4-difluorophenoxymethyl)-[1,2,4]-
    oxadiazol-3-yl]benzensulfonamide,
N-[4-[2-[[2-hydroxy-2-(3-pyridinyl)ethyl]amino]ethyl]
    phenyl]-4-[5-(3-acetamidophenoxymethyl)-[1,2,4]-
    oxadiazol-3-yl]benzensulfonamide,
N-[4-[2-[[2-hydroxy-2-(3-pyridinyl)ethyl]amino]ethyl]
    phenyl]-4-[5-(3-trifluoromethylphenoxymethyl)-[1,2,4]-
    oxadiazol-3-yl]benzensulfonamide,
N-[4-[2-[[2-hydroxy-2-(3-pyridinyl)ethyl]amino]ethyl]
    phenyl]-4-[5-(4-tetrazol-5-ylphenoxymethyl)]-[1,2,4]-
    oxadiazol-3-yl]benzensulfonamide,
N-[4-[2-[[2-hydroxy-2-(3-pyridinyl)ethyl]amino]ethyl]
    phenyl]-4-[5-(4-acetyloxyphenoxymethyl)-[1,2,4]-
    oxadiazol-3-yl]benzensulfonamide,
N-[4-[2-[[2-hydroxy-2-(3-pyridinyl)ethyl]amino]ethyl]
    phenyl]-4-[5-(4-methylphenoxymethyl)-[1,2,4]-
    oxadiazol-3-yl]benzensulfonamide,
N-[4-[2-[[2-hydroxy-2-(3-pyridinyl)ethyl]amino]ethyl]
    phenyl]-4-[5-(2-phenoxyethyl)-[1,2,4]-oxadiazol-3-yl]
    benzensulfonamide,
N-[4-[2-[[2-hydroxy-2-(3-pyridinyl)ethyl]amino]ethyl]
    phenyl]-4-[5-(phenylamino)-[1,2,4]-oxadiazol-3-yl]
    benzensulfonamide,
N-[4-[2-[[2-hydroxy-2-(3-pyridinyl)ethyl]amino]ethyl]
    phenyl]-4-[5-(4-fluorophenylamino)-[1,2,4]-oxadiazol-3-
    yl]benzensulfonamide,
N-[4-[2-[[2-hydroxy-2-(3-pyridinyl)ethyl]amino]ethyl]
    phenyl]-4-[3-(3,4-difluorophenylmethyl)-[1,2,4]-
    oxadiazol-5-yl]benzensulfonamide,
N-[4-[2-[[2-hydroxy-2-(3-pyridinyl)ethyl]amino]ethyl]
    phenyl]-4-[3-(4-fluorophenylmethyl)-[1,2,4]-oxadiazol-
    5-yl]benzensulfonamide,
N-[4-[2-[[2-hydroxy-2-(3-pyridinyl)ethyl]amino]ethyl]
    phenyl]-4-[5-(3,4-methylenedioxyphenylmethyl)-[1,2,4]-
    oxadiazol-3-yl]benzensulfonamide,
N-[4-[2-[[2-hydroxy-2-(3-pyridinyl)ethyl]amino]ethyl]
    phenyl]-4-[5-(4-fluorophenylcarbonyl)-[1,2,4]-
    oxadiazol-3-yl]benzensulfonamide,
N-[4-[2-[[2-hydroxy-2-(3-pyridinyl)ethyl]amino]ethyl]
    phenyl]-4-[5-(4-chlorophenylcarbonyl)-[1,2,4]-
    oxadiazol-3-yl]benzensulfonamide,
N-[4-[2-[[2-hydroxy-2-(3-pyridinyl)ethyl]amino]ethyl]
    phenyl]-4-[3-(4-fluorophenoxymethyl)-[1,2,4]-
    oxadiazol-5-yl]benzenesulfonamide,
N-[4-[2-[[2-hydroxy-2-(3-pyridinyl)ethyl]amino]ethyl]
    phenyl]-4-[5-(4-trifluoromethoxyphenoxymethyl,)-[1,2,
    4]-oxadiazol-3-yl]benzensulfonamide,
N-[4-[2-[[2-hydroxy-2-(3-pyridinyl)ethyl]amino]ethyl]
    phenyl]-4-[5-(4-trifluoromethoxyphenylmethyl)-[1,2,4]-
    oxadiazol-3-yl]benzensulfonamide,
N-[4-[2-[[2-hydroxy-2-(3-pyridinyl)ethyl]amino]ethyl]
    phenyl]-4-[5-[1-(4-fluorophenyl)-1-methoxymethyl]-[1,
    2,4]-oxadiazol-3-yl]benzenesulfonamide,
N-[4-[2-[[2-hydroxy-2-(3-pyridinyl)ethyl]amino]ethyl]
    phenyl]-4-[5-[1-(3,4-difluorophenyl)-1-methoxymethyl]-
    [1,2,4]-oxadiazol-3-yl]benzenesulfonamide,
N-[4-[2-[[2-hydroxy-2-(3-pyridinyl)ethyl]amino]ethyl]
    phenyl]-4-[5-[1-(4-fluorophenyl)-1-ethoxymethyl]-[1,2,
    4]-oxadiazol-3-yl]benzenesulfonamide,
N-[4-[2-[[2-hydroxy-2-(3-pyridinyl)ethyl]amino]ethyl]
    phenyl]-4-[5-[1-(4-chlorophenyl)-1-methoxymethyl]-[1,
    2,4]-oxadiazol-3-yl]benzenesulfonamide, and
N-[4-[2-[[2-hydroxy-2-(3-pyridinyl)ethyl]amino]ethyl]
    phenyl]-4-[5-[1-(4-chlorophenyl)-1-ethoxymethyl]-[1,2,
    4]-oxadiazol-3-yl]benzenesulfonamide,
N-[4-[2-[[2-hydroxy-2-(3-pyridinyl)ethyl]amino]ethyl]
    phenyl]-4-[5-(2-naphthyl)-[1,2,4]-oxadiazol-3-yl]
    benzenesulfonamide,
N-[4-[2-[[2-hydroxy-2-(3-pyridinyl)ethyl]amino]ethyl]
    phenyl]-4-[5-(6-quinolinyl)-[1,2,4]-oxadiazol-3-yl]
    benzenesulfonamide,
N-[4-[2-[[2-hydroxy-2-(3-pyridinyl)ethyl]amino]ethyl]
    phenyl]-4-[5-(3-methoxyphenoxymethyl)-[1,2,4]-
    oxadiazol-3-yl]benzenesulfonamide,
N-[4-[2-[[2-hydroxy-2-(3-pyridinyl)ethyl]amino]ethyl]
    phenyl]-4-[5-(3-chlorophenoxymethyl)-[1,2,4]-
    oxadiazol-3-yl]benzenesulfonamide,
N-[4-[2-[[2-hydroxy-2-(3-pyridinyl)ethyl]amino]ethyl]
    phenyl]-4-[5-(4-isopropylphenoxymethyl)-[1,2,4]-
    oxadiazol-3-yl]benzenesulfonamide,
N-[4-[2-[[2-hydroxy-2-(3-pyridinyl)ethyl]amino]ethyl]
    phenyl]-4-[5-(4-chlorophenoxymethyl)-[1,2,4]-
    oxadiazol-3-yl]benzenesulfonamide,
N-[4-[2-[[2-hydroxy-2-(3-pyridinyl)ethyl]amino]ethyl]
    phenyl]-4-[5-(3,4-dichlorophenoxymethyl)-[1,2,4]-
    oxadiazol-3-yl]benzenesulfonamide,
N-[4-[2-[[2-hydroxy-2-(3-pyridinyl)ethyl]amino]ethyl]
    phenyl]-4-[5-(4-tert-butylphenoxymethyl)-[1,2,4]-
    oxadiazol-3-yl]benzenesulfonamide,
N-[4-[2-[[2-hydroxy-2-(3-pyridinyl)ethyl]anuno]ethyl]
    phenyl]-4-[5-(4-sulfonarnidophenoxymethyl)-[1,2,4]-
    oxadiazol-3-yl]benzenesulfonamide,
N-[4-[2-[[2-hydroxy-2-(3-pyridinyl)ethyl]amino]ethyl]
    phenyl]-4-[5-(3-chloronaphthyl-1-yloxymethyl)-[1,2,4]-
    oxadiazol-3-yl]benzenesulfonamide,
N-[4-[2-[[2-hydroxy-2-(3-pyridinyl)ethyl]amino]ethyl]
    phenyl]-4-[5-(5-indanyloxymethyl)-[1,2,4]-oxadiazol-3-
    yl]benzenesulfonamide,
N-[4-[2-[[2-hydroxy-2-(3-pyridinyl)ethyl]amino]ethyl]
    phenyl]-4-[5-(4-indanyloxymethyl)-[1,2,4]-oxadiazol-3-
    yl]benzenesulfonamide,
N-[4-[2-[[2-hydroxy-2-(3-pyridinyl)ethyl]amino]ethyl]
    phenyl]-4-[5-(2-chlorophenoxymethyl)-[1,2,4]-
    oxadiazol-3-yl]benzenesulfonamide,
N-[4-[2-[[2-hydroxy-2-(3-pyridinyl)ethyl]amino]ethyl]
    phenyl]-4-[5-(3,5-dichlorophenoxymethyl)-[1,2,4]-
    oxadiazol-3-yl]benzenesulfonamide,
N-[4-[2-[[2-hydroxy-2-(3-pyridinyl)ethyl]amino]ethyl]
    phenyl]-4-[5-(3-trifluoromethoxyphenoxymethyl)-1,2,4]-
    oxadiazol-3-yl]benzenesulfonamide,
N-[4-[2-[[2-hydroxy-2-(3-pyridinyl)ethyl]amino]ethyl]
    phenyl]-4-[5-[4-(1,2-benzisoxazol-3-yl)-2,3-
    dichlorophenoxymethyl]-[1,2,4]-oxadiaxol-3-yl]
    benzenesulfonamide,
N-[4-[2-[[2-hydroxy-2-(3-pyridinyl)ethyl]amino]ethyl]
    phenyl]-4-[5-(2,4-dichlorophenoxymethyl)-[1,2,4]-
    oxadiazol-3-yl]benzenesulfonamide,
N-[4-[2-[[2-hydroxy-2-(3-pyridinyl)ethyl]amino]ethyl]
    phenyl]-4-[5-[4-(2-quinazolinyl)phenoxymethyl]-[1,2,4]-
    oxadiazol-3-yl]benzenesulfonamide,
N-[4-[2-[[2-hydroxy-2-(3-pyridinyl)ethyl]amino]ethyl]
    phenyl]-4-[5-(2,4,5-trichlorophenoxymethyl)-[1,2,4]-
    oxadiazol-3-yl]benzenesulfonamide,
N-[4-[2-[[2-hydroxy-2-(3-pyridinyl)ethyl]amino]ethyl]
    phenyl]-4-[5-(2,3-dichlorophenoxymethyl)-[1,2,4]-
    oxadiazol-3-yl]benzenesulfonamide,
N-[4-[2-[[2-hydroxy-2-(3-pyridinyl)ethyl]amino]ethyl]
    phenyl]-4-[5-(2-chloro-4-tert-butylphenoxymethyl)-[1,2,
    4]-oxadiazol-3-yl]benzenesulfonamide,
N-[4-[2-[[2-hydroxy-2-(3-pyridinyl)ethyl]amino]ethyl]
    phenyl]-4-[5-[2,3-dichloro-4-(2-thienylsulfonyl)
    phenoxymethyl]-[1,2,4]-oxadiaxol-3-yl]
    benzenesulfonamide, N-[4-[2-[[2-hydroxy-2-(3-pyridinyl)ethyl]amino]ethyl]
phenyl]-4-[5-[4-(N,N-dipropylsulfamoyl)
phenoxymethyl]-[1,2,4]-oxadiazol-3-yl]
benzenesulfonamide, N-[4-[2-[[2-hydroxy-2-(3-pyridinyl)ethyl]amino]ethyl]
phenyl]-4-[5-(4-trifluoromethylphenyl)-[1,2,4]-
oxadiazol-3-yl]benzenesulfonamide, N-[4-[2-[[2-hydroxy-2-(3-pyridinyl)ethyl]amino]ethyl]
phenyl]-4-[5-(4-trifluoromethoxyphenyl)-[1,2,4]-
oxadiazol-3-yl]benzenesulfonamide, N-[4-[2-[[2-hydroxy-2-(3-pyridinyl)ethyl]amino]ethyl]
phenyl]-4-[5-(3,4,5-trifluorophenyl)-[1,2,4]-oxadiazol-3-
yl]benzenesulfonamide, N-[4-[2-[[2-hydroxy-2-(3-pyridinyl)ethyl]amino]ethyl]
phenyl]-4-[5-(6-fluoronaphth-2-yloxymethyl,)-[1,2,4]-
oxadiazol-3-yl]benzenesulfonamide, N-[4-[2-[[2-hydroxy-2-(3-pyridinyl)ethyl]amino]ethyl]
phenyl]-4-[5-(6-fluoronaphth-2-ylmethyl,)-[1,2,4]-
oxadiazol-3-yl]benzenesulfonamide, N-[4-[2-[[2-hydroxy-2-(pyridin-3-yl)ethyl]amino]ethyl]
phenyl]-4-[5-[1-fluoro-1-(4-trifluoromethylphenyl)
methyl]-[1,2,4]-oxadiazol-3-yl]benzenesulfonamide, N-[4-[2-[[2-hydroxy-2-(pyridin-3-yl)ethyl]amino]ethyl]
phenyl]-4-[5-[1-(4-trifluoromethylphenyl)-1-ethyl]-[1,2,
4]-oxadiazol-3-yl]benzenesulfonamide, N-[4-[2-[[2-hydroxy-2-(pyridin-3-yl)ethyl]amino]ethyl]
phenyl]-4-[5-[    ]-[1,2,4]-oxadiazol-3-yl]
benzenesulfonamide, N-[4-[2-[[2-hydroxy-2-(pyridin-3-yl)ethyl]amino]ethyl]
phenyl]-4-[5-[    ]-[1,2,4]-oxadiazol-3-yl]
benzenesulfonamide, N-[4-[2-[[2-hydroxy-2-(pyridin-3-yl)ethyl]amino]ethyl]
phenyl]-4-[5-[    ]-[1,2,4]-oxadiazol-3-yl]
benzenesulfonamide, N-[4-[2-[[2-hydroxy-2-(pyridin-3-yl)ethyl]amino]ethyl]
phenyl]-4-[5-[    ]-[1,2,4]-oxadiazol-3-yl]
benzenesulfonamide, N-[4-[2-[[2-hydroxy-2-(pyridin-3-yl)ethyl]amino]ethyl]
phenyl]-4-[5-[1-(4-fluorophenoxy)-1-methylethyl]-[1,2,
4]-oxadiazol-3-yl]benzenesulfonamide, N-[4-[2-[[2-hydroxy-2-(pyridin-3-yl)ethyl]amino]ethyl]
phenyl]-4-[5-[1-(1-naphthyloxy)-1-methylethyl]-[1,2,4]-
oxadiazol-3-yl]benzenesulfonamnide, N-[4-[2-[[2-hydroxy-2-(pyridin-3-yl)ethyl]amino]ethyl]
phenyl]-4-[5-[1-(2-naphthyloxy)-1-methylethyl]-[1,2,4]-
oxadiazol-3-yl]benzenesulfonamide, N-[4-[2-[[2-hydroxy-2-(pyridin-3-yl)ethyl]amino]ethyl]
phenyl]-4-[5-[1-(4-chlorophenoxy)-1-methylethyl]-[1,2,
4]-oxadiazol-3-yl]benzenesulfonamide, N-[4-[2-[[2-hydroxy-2-(pyridin-3-yl)ethyl]amino]ethyl]
phenyl]-4-[5-[1-(2-chlorophenoxy)-1-methylethyl]-[1,2,
4]-oxadiazol-3-yl]benzenesulfonamide, N-[4-[2-[[2-hydroxy-2-(pyridin-3-yl)ethyl]amino]ethyl]
phenyl]-4-[5-[1,1-difluoro-1-(phenyl)methyl]-[1,2,4]-
oxadiazol-3-yl]benzenesulfonamide, N-[4-[2-[[2-hydroxy-2-(pyridin-3-yl)ethyl]amino]ethyl]
phenyl]-4-[5-[1-(4-(4-chlorophenyl)phenoxy)-1-
methylethyl]-[1,2,4]-oxadiazol-3-yl]
benzenesulfonamide, N-[4-[2-[[2-hydroxy-2-(pyridin-3-yl)ethyl]amino]ethyl]
phenyl]-4-[5-[1-(4-chlorophenyl)-1-methylethyl]-[1,2,4]-
oxadiazol-3-yl]benzenesulfonamide, N-[4-[2-[[2-hydroxy-2-(pyridin-3-yl)ethyl]amino]ethyl]
phenyl]-4-[5-[1-(4-trifluoromethoxyphenyl)-1-ethyl]-[1,
2,4]-oxadiazol-3-yl]benzenesulfonamide, N-[4-[2-[[2-hydroxy-2-(pyridin-3-yl)ethyl]amino]ethyl]
phenyl]-4-[5-[1-fluoro-1-(4-trifluoromethoxyphenyl)
methyl]-[1,2,4]-oxadiazol-3-yl]benzenesulfonamide, N-[4-[2-[[2-hydroxy-2-(pyridin-3-yl)ethyl]amino]ethyl]
phenyl]-4-[5-[1-(6-fluoronaphth-2-yl)-1-
hydroxymethyl]-[1,2,4]-oxadiazol-3-yl]
benzenesulfonamide, N-[4-[2-[[2-hydroxy-2-(pyridin-3-yl)ethyl]amino]ethyl]
phenyl]-4-[5-[1-(6-fluoronaphth-2-yl)-1-ethyl]-[1,2,4]-
oxadiazol-3-yl]benzenesulfonamide, N-[4-[2-[[2-hydroxy-2-(pyridin-3-yl)ethyl]amino]ethyl]
phenyl]-4-[5-[1-(6-fluoronaphth-2-yl)-1-methylethyl]-[1,
2,4]-oxadiazol-3-yl]benzenesulfonamide, N-[4-[2-[[2-hydroxy-2-(pyridin-3-yl)ethyl]amino]ethyl]
phenyl]-4-[3-(4-trifluoromethylphenyl)-[1,2,4]-
oxadiazol-5-yl]benzenesulfonamide, N-[4-[2-[[2-hydroxy-2-(pyridin-3-yl)ethyl]amino]ethyl]
phenyl]-4-[3-(4-trifluoromethoxyphenyl)-[1,2,4]-
oxadiazol-5-yl]benzenesulfonamide.

The compounds of the instant invention all have at least one asymmetric center as noted by the asterisk in structural Formula I. Additional asymmetric centers may be present on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the hydroxy substituent is above the plane of the structure, as seen in Formula Ic, is more active and thus more preferred over the compound in which the hydroxy substituent is below the plane of the structure.

The following stereospecific structure represents the preferred stereoisomers of the instant invention:

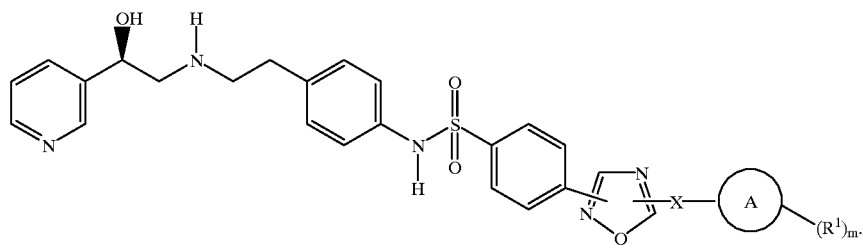

Ic

Throughout the instant application, the following terms have the indicated meanings:

"Alkylene" means —$(CH_2)_p$— where p is the designated carbon number. Optionally substituted alkylene may have one or two of the hydrogen atoms replaced with the same or different enumerated substituents. Where the alkylene contains up to two groups selected from Q, and carbonyl, the Q. or carbonyl group may be at either end of the alkylene chain, or it may be embedded within the chain. Examples include $OCH(CH_3)$, $OC(CH_3)_2$, $C(CH_3)_2O$, $OCH_2$, $CH_2O$, $C(O)CH_2$, $CH_2OCH_2$, $OC(O)CH_2$, $OCH_2CH_2C(O)$, $OCH_2CH_2O$, $OCH_2CH_2C(O)CHCH_2$, $CH_2CH(OCH_3)CH_2$, $CH(OCH_3)CH_2$, etc.

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atoms fluorine, chlorine, bromine and iodine.

The term "carbocyclic ring" is intended to include both aromatic and nonaromatic rings containing only carbon atoms. Thus, a benzene ring fused to a $C_5$–$C_{10}$ carbocyclic ring, includes naphthyl, tetrahydronaphthyl, indanyl and indenyl. A 5 or 6-membered heterocyclic ring with from 1 to 4 heteroatoms selected from oxygen, sulfur and nitrogen fused to a $C_5$–$C_{10}$ carbocyclic ring includes benzene fused to a heterocyclic ring as well as a non-aromatic carbocyclic ring fused to a heterocyclic ring. The carbocyclic ring preferably is $C_5$–$C_7$.

A 5 and 6-membered heterocyclic ring, whether isolated or as a part of a fused ring system, is intended to include aromatic and unsaturated non-aromatic heterocycles; and where the heterocycle is part of a fused ring, at least one of the rings is aromatic. Examples of a 5 or 6-membered ring include pyridyl, pyrimidinyl, pyrrolyl, furyl, thienyl, imidazolyl, thiazolyl, thiadiazolyl, tetrazolyl, oxadiazolyl, oxazolyl, imidazolidinyl, pyrazolyl, isoxazolyl. Examples of a benzene ring fused to a 5 or 6-membered heterocyclic ring include benzothiadiazolyl, indolyl, indolinyl, benzodioxolyl, benzodioxanyl, benzothiophenyl, benzofuranyl, benzimidazolyl, benzoxazinyl, benzisoxazolyl, benzothiazolyl, 2,3-dihydrobenzofuranyl, quinolinyl, benzotriazolyl, benzoxazolyl, 1,2,3,4-tetrahydroisoquinolinyl, 1,2,3,4-tetrahydroquinolinyl. Examples of a 5 or 6-membered heterocyclic ring fused to a 5 or 6-membered heterocyclic ring incude purinyl, furopyridine and thienopyridine. Examples of a 5 or 6-membered heterocyclic ring fused to a non-aromatic carbocyclic ring include tetrahydrobenzothiazolyl, 5,6,7,8-tetrahydroquinolinyl, 2,3-cyclopentenopyridyl, 4,5,6,7-tetrahydroindolyl, 5,6,7,8-tetrahydroisoquinolyl, 5,6,7,8-tetrahydroquinoxalinyl.

The preferred values of A are phenyl, naphthyl, benzene ring fused to a 5 or 6-membered heterocyclic ring with from 1 to 4 heteroatoms selected from oxygen, sulfur and nitrogen, or heterocycles with from 1 to 4 heteroatoms independently selected from one of oxygen or sulfur, and/or 1 to 4 nitrogen atoms.

The more preferred values of A are phenyl, naphthyl, thienyl, pyridinyl, pyrrolyl, benzothienyl, and 2,3-dihydrobenzofuranyl.

Certain of the above defined terms may occur more than once in the above formula and upon such occurrence each term shall be defined independently of the other; thus for example, $NR^2R^2$ may represent $NH_2$, $NHCH_3$, $N(CH_3)CH_2CH_3$, and the like.

The following abbreviations are used throughout the specification:

AcOH: acetic acid
AR: adrenergic receptor
Boc/BOC: tert-butyloxycarbonyl
CHO: Chinese hamster ovary
DBU: 1,8-diazabicyclo[5.4.0]undec-7-ene
DCC: dicyclohexycarbodiimide
DCM: dichloromethane
DIEA: diisopropylethylamine
DMF: dimethylformamide
EDC: 1-(3-dimethylaminopropyl)-3-ethylcarbodiimide
EtOAc: ethyl acetate
HPLC: high pressure liquid chromatography
iPrOH: isopropyl alcohol
NMR: nuclear magnetic resonance
TES: triethylsilyl
TFA: trifluoroacetic acid
THF: tetrahydrofuran
TLC: thin layer chromatography The compounds (I) of the present invention can be prepared as described in the following schemes. For oxadiazoles Ia where X is other than Q or Q-$C_1$–$C_3$ alkylene, as illustrated in Scheme 1, the protected aniline derivative 1 (See Fisher, et. al., WO9529159-A, Nov. 2, 1995, for the synthesis of this compound.) is treated with a 4-cyanobenzenesulfonyl halide, conveniently the sulfonyl chloride 2, and a base such as pyridine in an anhydrous solvent such as dichloromethane or chloroform for 0.5 to 24 hours at temperatures of −20 to 50° C., preferably 0° C., to provide the sulfonamide 3. Treatment of sulfonamide 3 with hydroxylamine, which may be formed in situ from hydroxylamine hydrochloride and a base such as potassium carbonate, in a solvent such as ethanol at temperatures from 0° C. to 100° C., conveniently 70–80° C., provides the corresponding amidoxime 4. The oxadiazole is then formed by methods known in the literature (See, for example, Borg, et. al., J. Org. Chem. 1995, 60, 3112–3120 and Diana, et. al., J. Med. Chem. 1994, 37, 2421–2436, and references cited therein). This is conveniently carried out by acylation with an acid halide such as the acid chloride 5 (X=Cl) or an anhydride 5 (X=OCOR) including mixed anhydrides in the presence of base or with an acid 5 (X=OH) and a peptide coupling reagent such as ethyldimethylaminopropylcarbodiimide, followed by heating to effect cyclization in a solvent such as pyridine or diglyme. Removal of the protecting group with, in the case of a tert-butylcarbamate, acid such as trifluoroacetic acid or methanolic hydrogen chloride, provides the oxadiazole Ia. The carboxylic acids or acid derivatives 5 are commercially available, known in the literature, or readily prepared by methods commonly known to those skilled in the art.

In some cases, the product Ia from the reaction described in Scheme 1 may be further modified, for example, by the removal of protecting groups or the manipulation of substituents on $R^1$. These manipulations may include, but are not limited to, reduction, oxidation, alkylation, acylation, and hydrolysis reactions which are commonly known to those skilled in the art.

SCHEME 1

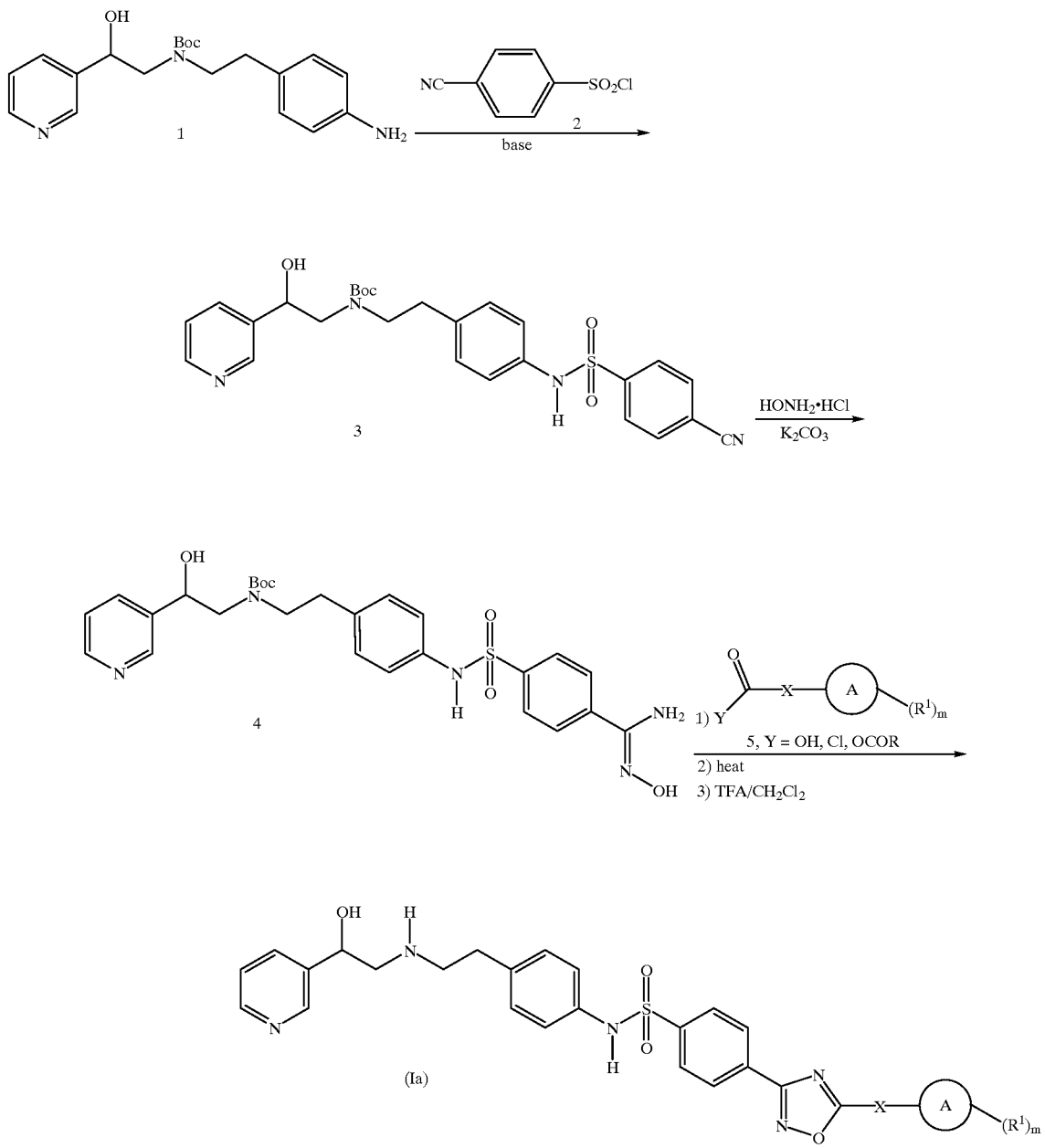

The method employed in Scheme 1 relies on masking the secondary amine in the final product as an N-Boc derivative. Alternate protecting groups for this secondary amine, which are readily known to those skilled in the art, may be employed. In addition, the reactions illustrated in Scheme 1 may be carried out on a solid phase support linkage. This approach is illustrated in Schemes 2 and 3. As shown in Scheme 2, aniline derivative 6 is coupled to a solid support such as NovaSyn® TGA resin from Novabiochem (7) by treatment with an activating agent, conveniently 4-nitrophenyl chloroformate in the presence of base such as diisopropylethylamine in a solvent or solvent mixture such as 1:1 tetrahydrofuran/dichloromethane. The hydroxyl group is then protected, conveniently as its triethylsilyl ether using triethylsilyl chloride in the presence of a base such as diisopropylethylamine. The resultant derivative 8 is treated with 4-cyanobenzenesulfonyl halide, conveniently the sulfonyl chloride 2, in the presence of a base such as pyridine, to provide the sulfonamide 9. Treatment of intermediate 9 with hydroxylamine as described above provides the corresponding amidoxime 10.

SCHEME 2

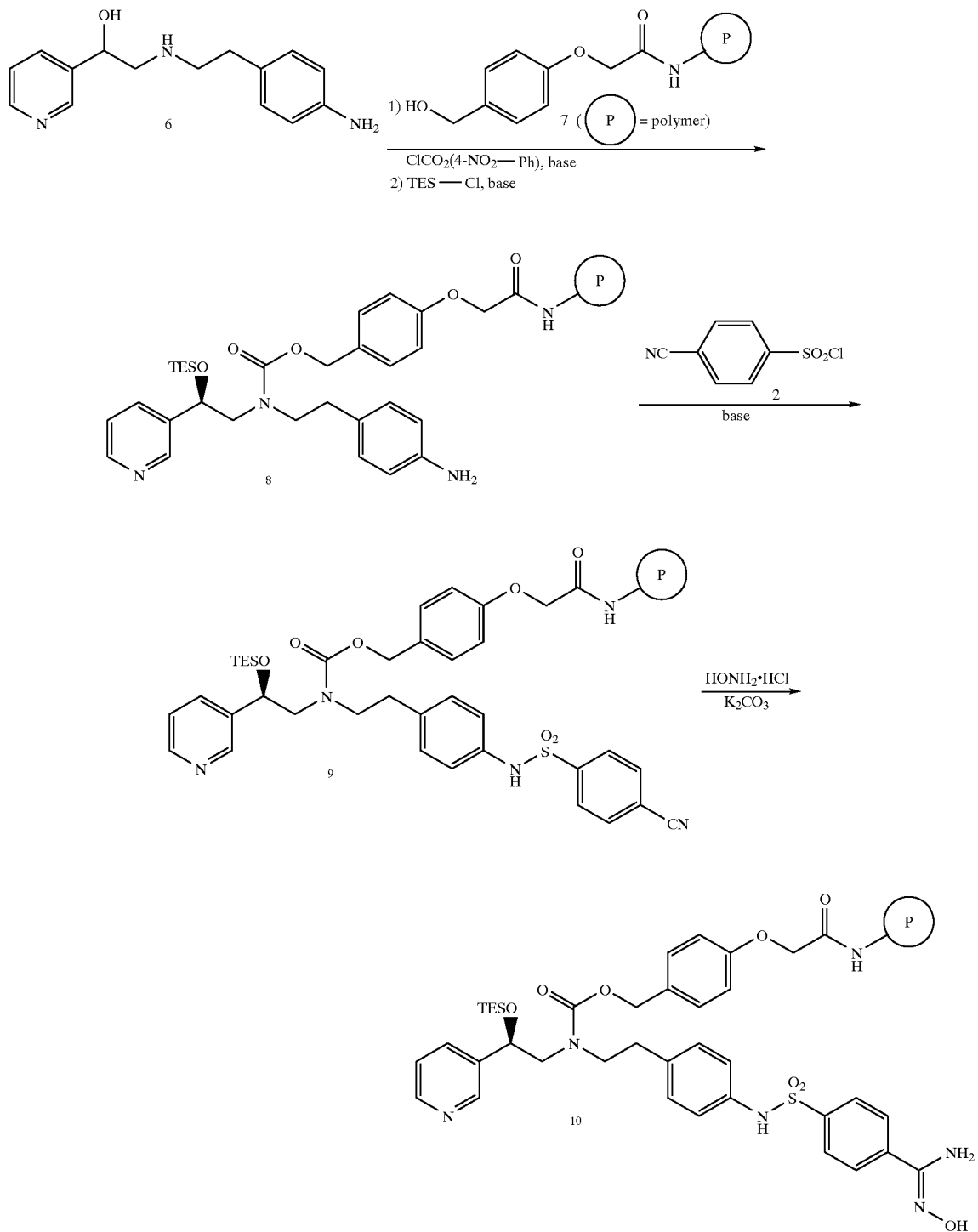

The oxadiazoles Ia are prepared from intermediate 10 as illustrated in Scheme 3. Treatment of the resin-bound amidoxime with an acid, acid chloride or anhydride 5 as described above, in a solvent such as diglyme with heating, conveniently to 90–110° C., gives the resin-bound oxadiazole. Cleavage from the resin is effected, in the case of Novasyn TGA resin from Novabiochem, by treatment with acid such as trifluoroacetic acid as a 1:1 mixture with dichloromethane.

SCHEME 3

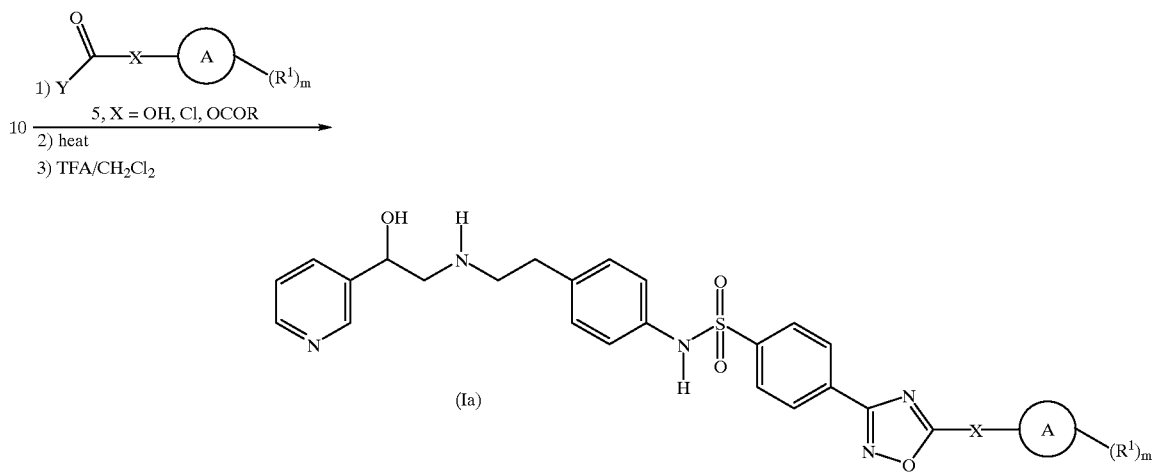

For cases where X=NH in Formula Ia, the oxadiazole may be prepared from the corresponding isocyanidedichloride (See for example, Japan Patent 05117255, 1993). As shown in Scheme 4, intermediate 4 is treated with isocyanidedichloride 11 and a base such as DBU. Removal of the Boc protecting group under acidic conditions, for example, with trifluoroacetic acid in dichloromethane, provides the desired oxadiazoles Ia. The requisite isocyanidedichlorides 11 are known in the literature (for example, Kuhle, Angew. Chem. 1962, 74, 861–866) or readily prepared by methods known to those skilled in the art.

SCHEME 4

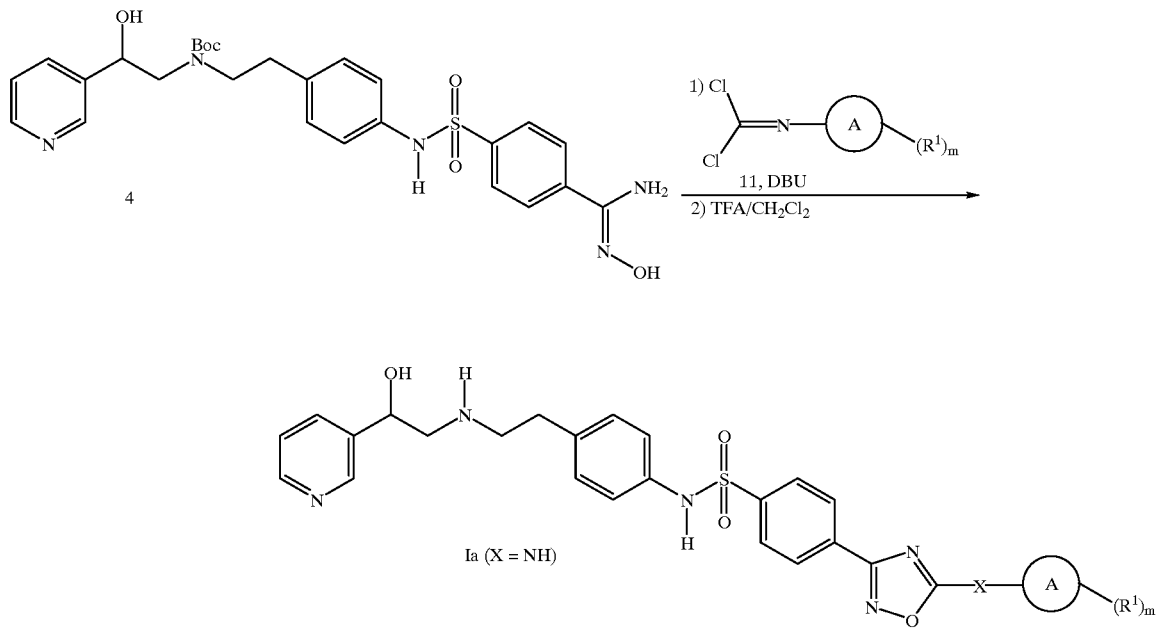

For cases where X contains a sulfur or oxygen directly attached to the oxadiazole ring, compounds Ia may be prepared by reaction of the corresponding thiol or alcohol with an activated oxadiazole. As shown in Scheme 5, the amidoxime 4 is treated with trichloroacetyl chloride in a base such as pyridine followed by heating to provide the corresponding oxadiazole 12. Displacement of the trichlo romethyl group with an alcohol or thiol 13 in the presence of a base and subsequent deprotection of the Boc secondary amine with acid such as trifluoroacetic acid gives the desired oxadiazoles Ia.

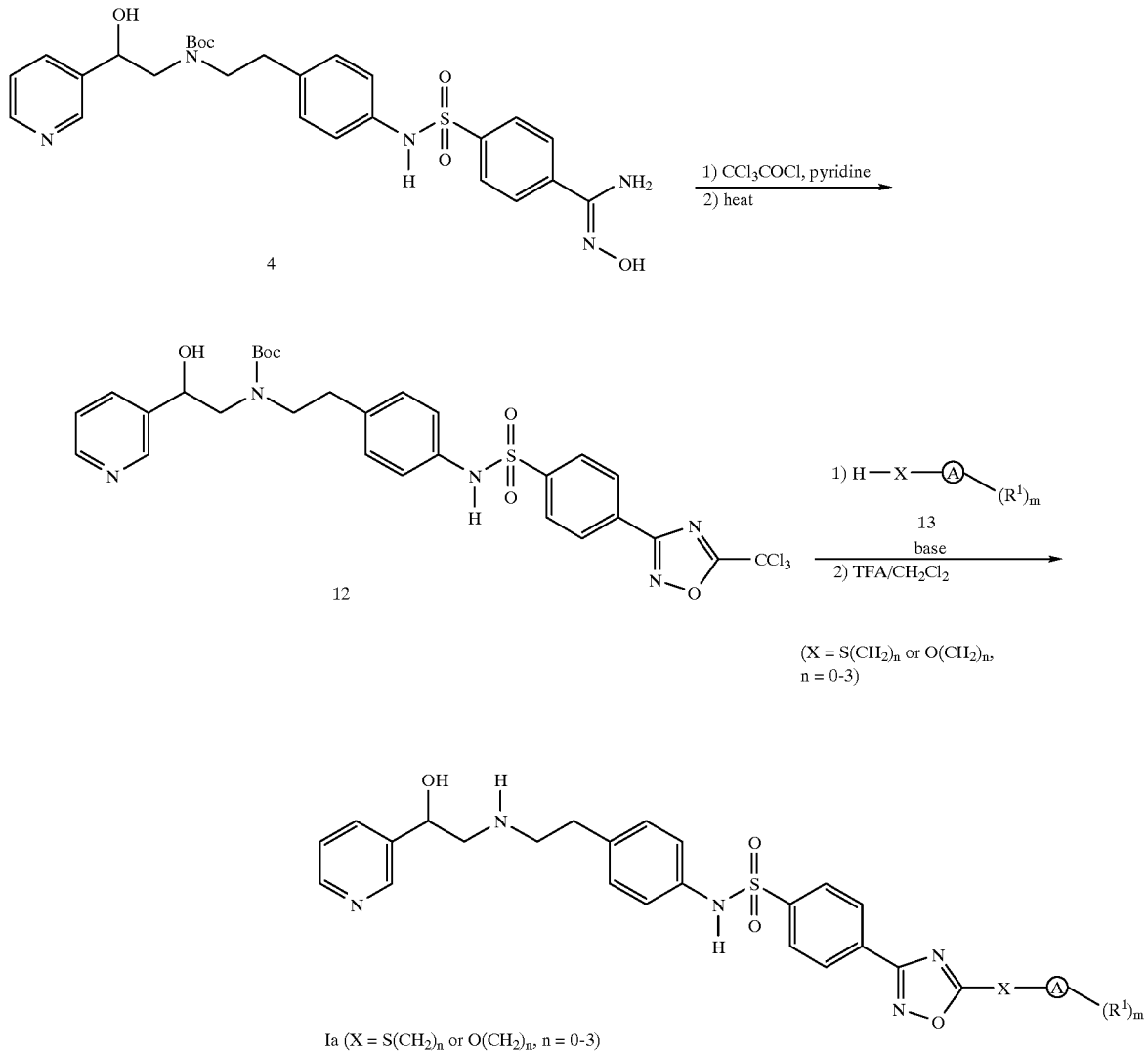

SCHEME 5

In some cases, the product Ia from the reactions described in Schemes 4 and 5 may be further modified, for example, by the removal of protecting groups or the manipulation of substituents on $R^1$. These manipulations may include, but are not limited to, reduction, oxidation, alkylation, acylation, and hydrolysis reactions which are commonly known to those skilled in the art.

The isomeric oxadiazoles Ib are readily available as illustrated in Scheme 6. Aniline derivative 1 is sulfonylated by treatment with 4-(chlorosulfonyl)benzoic acid (14) in the presence of a base such as pyridine to provide the corresponding sulfonamide 15. The oxadiazole is then formed as described above by treatment of 15 with the appropriate amidoxime 16 in the presence of a peptide coupling reagent such as dicyclohexylcarbodiimide or N-ethyl-N'-dimethylaminopropylcarbodiimide, followed by heating to effect cyclization in a solvent such as pyridine or diglyme.

Removal of the protecting group with, in the case of a tert-butylcarbamate, acid such as trifluoroacetic acid or methanolic hydrogen chloride, provides the oxadiazole Ib. The amidoximes 16 are commercially available, known in the literature, or readily prepared by methods commonly known to those skilled in the art. Conveniently, they are prepared from the corresponding nitrile by treatment with hydroxylamine.

In some cases, the product Ib from the reaction described in Scheme 6 may be further modified, for example, by the removal of protecting groups or the manipulation of substituents on $R^1$. These manipulations may include, but are not limited to, reduction, oxidation, alkylation, acylation, and hydrolysis reactions which are commonly known to those skilled in the art.

SCHEME 6

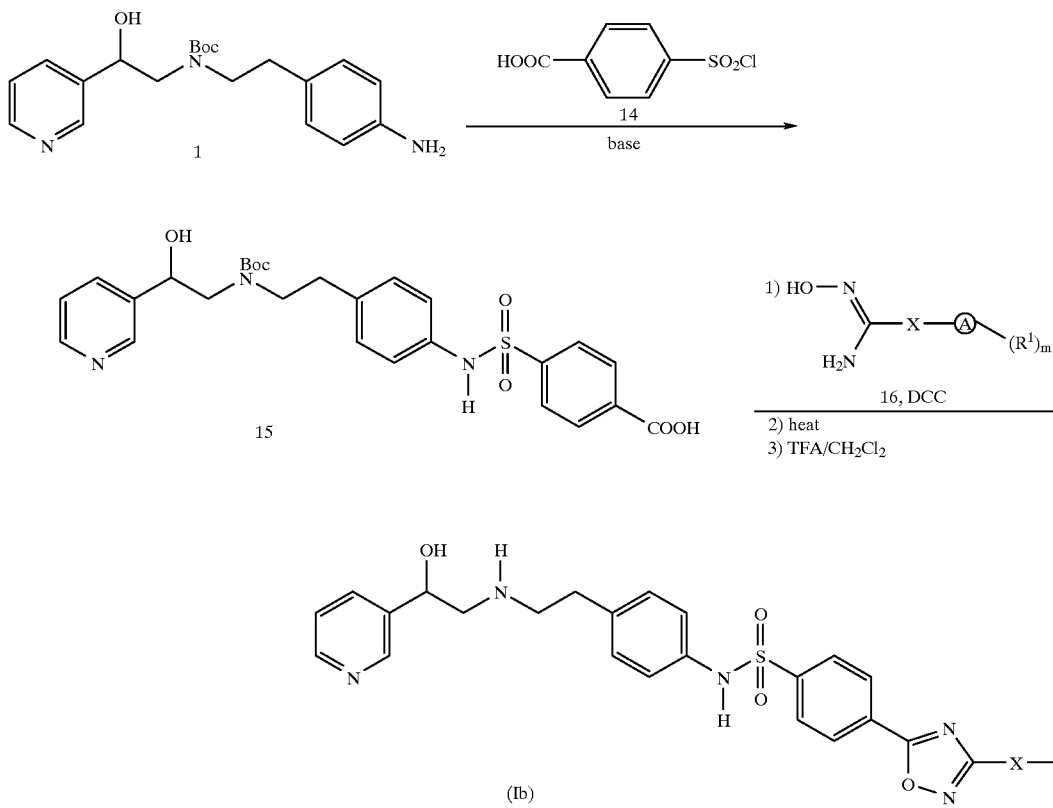

An alternate approach to compounds Ib which involves the coupling of an oxadiazolylbenzenesulfonyl chloride to the aniline intermediate 1 is shown in Scheme 7. Amidoxime 16 is coupled to a protected 4-aminobenzoic acid derivative such as Boc-protected amine 17 using a coupling reagent such as EDC or DCC, followed by heating to effect ring closure. The resultant oxadiazole 18 is treated, in the case of a N-Boc-protected derivative, with trifluoroacetic acid. The resultant aniline is diazatized with, for example, sodium nitrite and then treated with sulfur dioxide and copper(I) chloride to provide the corresponding sulfonyl chloride 19. Coupling of sulfonyl chloride 19 and aniline intermediate 1 in the presence of base such as pyridine followed by deprotection with trifluoroacetic acid gives the desired oxadiazoles Ib.

SCHEME 7

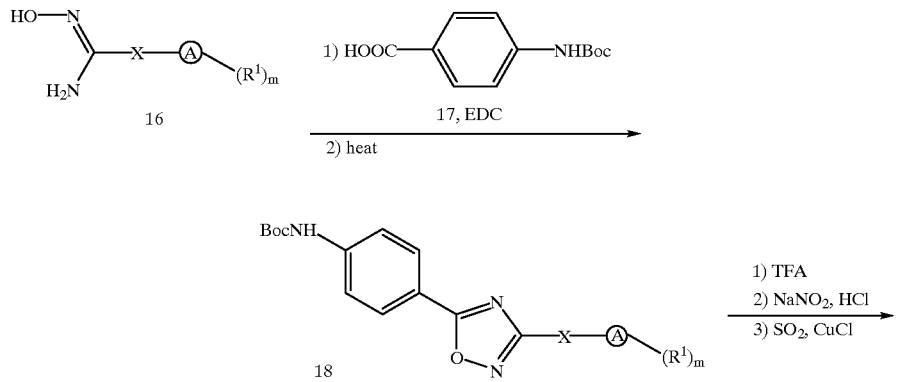

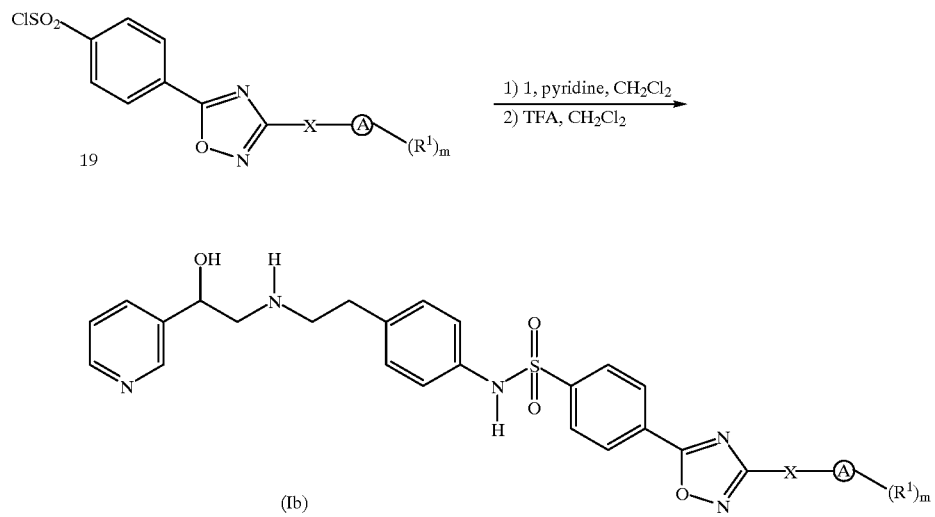

(Ib)

Compounds of the general Formula I may be present as pairs of enantiomers or, where there is more than one chiral centers, as mixtures of diastereomers. Enantiomeric pairs may be separated into individual stereoisomers by conventional means, for example by the use of an optically active acid as a resolving agent. A mixture of diastereomers may be separated into diastereoisomeric pairs of enantiomers by, for example, fractional crystallization from a suitable solvent, for example methanol or ethyl acetate or a mixture thereof. The pair of enantiomers may be separated as described above.

Alternatively, any enantiomer of a compound of the general Formula I may be obtained by stereospecific synthesis using optically pure starting materials of known configuration.

The instant compounds can be isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy or tetrazole, can be isolated in the form of their inorganic salt in which the counterion can be selected from sodium, potassium, lithium, calcium, magnesium and the like, as well as from organic bases.

As previously indicated, the compounds of the present invention have valuable pharmacological properties. Thus the present invention also provides a compound of the general Formula I or a pharmaceutically acceptable salt thereof for use as an active therapeutic substance.

The disease diabetes mellitus is characterized by metabolic defects in production and utilization of glucose which result in the failure to maintain appropriate blood sugar levels. The result of these defects is elevated blood glucose or hyperglycemia. Research on the treatment of diabetes has centered on attempts to normalize fasting and postprandial blood glucose levels. Treatments have included parenteral administration of exogenous insulin, oral administration of drugs and dietary therapies.

Two major forms of diabetes mellitus are now recognized. Type I diabetes, or insulin-dependent diabetes, is the result of an absolute deficiency of insulin, the hormone which regulates glucose utilization. Type II diabetes, or insulin-independent diabetes, often occurs in the face of normal, or even elevated levels of insulin and appears to be the result of the inability of tissues to respond appropriately to insulin. Most of the Type II diabetics are also obese.

Compounds of the present invention are capable of stimulating β3 adrenoceptor mediated lipolysis, and lowering blood glucose levels. Thus, in one aspect, the present invention provides a compound of the general Formula I or a pharmaceutically acceptable salt thereof for use in the treatment of obesity or hyperglycemia (diabetes) in human or non-human animals. In another aspect, the present invention provides a method for the treatment of obesity which comprises administering to an obese patient a therapeutically effective amount of a compound of the general Formula I, or a pharmaceutically acceptable salt thereof. In a further aspect, the present invention provides a method for the treatment of diabetes which comprises administering to a diabetic patient a therapeutically effective amount of a compound of formula I.

In addition the compounds of the present invention lower triglyceride levels and cholesterol levels and raise high density lipoprotein levels and are therefore of use in combatting medical conditions wherein such lowering (and raising) is thought to be beneficial. Thus they may be used in the treatment of hypertriglyceridaemia, hypercholesterolaemia and conditions of low HDL (high density lipoprotein) levels in addition to the treatment of atherosclerotic disease such as of coronary, cerebrovascular and peripheral arteries, cardiovascular disease and related conditions.

Accordingly, in another aspect the present invention provides a method of lowering triglyceride and/or cholesterol levels and/or increasing high density lipoprotein levels which comprises administering, to a human or a non-human animal in need thereof, a therapeutically effective amount of a compound of the formula (I) or pharmaceutically acceptable salt thereof. In a further aspect the present invention provides a method of treating atherosclerosis which comprises administering, to an animal in need thereof; a therapeutically effective amount of a compound of the formula (I) or pharmaceutically acceptable salt thereof. The compositions are formulated and administered in the same general manner as detailed below for treating diabetes and obesity. They may also contain other active ingredients known for use in the treatment of atherosclerosis and related conditions, for example fibrates such as clofibrate, bezafibrate and gemfibrozil; inhibitors of cholesterol biosynthesis such as HMG-CoA reductase inhibitors for example lovastatin, simvastatin and pravastatin; inhibitors of cholesterol absorption for example beta-sitosterol and (acyl CoA-:cholesterol acyltransferase) inhibitors for example melinamide; anion exchange resins for example cholestyramine, colestipol or a dialkylaminoalkyl derivatives of a cross-linked dextran; nicotinyl alcohol, nicotinic acid or a salt thereof; vitamin E; and thyromimetics.

The compounds of the instant invention also have the effect of reducing intestinal motility and thus find utility as aiding in the treatment of various gastrointestinal disorders such as irritable bowel syndrome. It has been proposed that the motility of non-sphincteric smooth muscle contraction is mediated by activity at $\beta_3$ adrenoreceptors. The availability of a $\beta_3$ specific agonist, with little activity at $\beta_1$ and $\beta_2$ receptors will assist in the pharmacologic control of intestinal motility without concurrent cardiovascular effects. The instant compounds are administered generally as described below with dosages similar to those used for the treatment of diabetes and obesity.

It has also been found unexpectedly that the compounds which act as agonists at β3 adrenoreceptors may be useful in the treatment of gastrointestinal disorders, especially peptic ulcerations, esophagitis, gastritis and duodenitis, (including that induced by *H. pylori*), intestinal ulcerations (including inflammatory bowel disease, ulcerative colitis, Crohn's disease and proctitis) and gastrointestinal ulcerations.

In addition, $\beta_3$ receptors have been indicated to have an effect on the inhibition of the release of neuropeptides in certain sensory fibers in the lung. As sensory nerves may play an important role in the neurogenic inflammation of airways, including cough, the instant specific $\beta_3$ agonists may be useful in the treatment of neurogenetic inflammation, such as asthma, with minimal effects on the cardiopulmonary system.

$\beta_3$ adrenoreceptors are also able to produce selective antidepressant effects by stimulating the $\beta_3$ receptors in the brain and thus an additional contemplated utility of the compounds of this invention are as antidepressant agents.

The active compounds of the present invention may be orally administered as a pharmaceutical composition, for example, with an inert diluent, or with an assimilable edible carrier, or they may be enclosed in hard or soft shell capsules, or they may be compressed into tablets, or they may be incorporated directly with the food of the diet. For oral therapeutic administration, which includes sublingual administration, these active compounds may be incorporated with excipients and used in the form of tablets, pills, capsules, ampules, sachets, elixirs, suspensions, syrups, and the like. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The effective dosage of active ingredient employed may vary depending on the particular compound employed, the mode of administration, the condition being treated and the severity of the condition being treated.

When treating diabetes mellitus and/or hyperglycemia generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

When treating obesity, in conjunction with diabetes and/or hyperglycemia, or alone, generally satisfactory results are obtained when the compounds of the present invention are administered at a daily dosage of from 0.01 milligram to about 100 milligrams per kilogram of animal body weight, preferably given in a single dose or in divided doses two to six times a day, or in sustained release form. In the case of a 70 kg adult human, the total daily dose will generally be from about 0.7 milligrams to about 3500 milligrams. This dosage regimen may be adjusted to provide the optimal therapeutic response.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contabanating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The following in vitro assays are suitable for screening compounds that have selective β3 agonist activity:

Functional Assay: cAMP production in response to ligand is measured according to Barton et al (1991, Agonist-induced desensitization of D2 dopamine receptors in human Y-79 retinoblastoma cells. Mol. Pharmacol. v3229:650–658) modified as follows. CHO cells, stably transfected with the cloned β-adrenergic receptor ($\beta_1$, $\beta_2$ or $\beta_3$) are harvested after 3 days of subculturing. Harvesting is done with Enzyme-free Dissociation Media (Specialty Media). Cells are counted and distributed in the assay tubes, after being resuspended in Tris buffer (ACC buffer: 75 mM Tris, pH 7.4, 250 mM Sucrose, 12.5 mM $MgCl_2$, 1.5 mM EDTA, 0.2 mM Sodium Metabisulfite, 0.6 mM IBMX) containing an antioxidant and a phosphodiesterase inhibitor. Reaction is initiated by mixing 200,000 cells in 100 μL with 20 μL of a 6x stock of ligand/unknown to be tested. Tubes shake at 275 rpm for 45 min at room temperature. The reaction is stopped by boiling the tubes for 3 min. The cell lysate is diluted 5-fold in 0.1N HCl and then acetylated by the mixture of 150 μL of acid-diluted sample with 6 μL of acetylation mixture (acetic anhydride/triethylamine, 1:2.5). The cAMP produced in response to the ligand is measured in the lysate by competing against $^{125}$I-cAMP for binding to a $^{125}$I-cAMP-directed antibody using an automated RIA machine (ATTOFLO, Atto Instruments, Baltimore, Md., Brooker et al 1979, Radioimmunoassay of Cyclic AMP and Cyclic GMP. Advances in Cyclic Nucleotide Research. vol 10:1–32.). The unknown cAMP level is determined by comparing levels to a standard curve. Alternatively, cAMP is measured using the cAMP SPA kit (code number RPA 556) from Amersham according to the manufacturer's instructions. Samples tested with the latter method do not need to be acetylated.

The non-selective, full agonist β-adrenergic ligand isoproterenol is used at all three receptors to deternine maximal stimulation. The human β3 AR-selective ligand (S)-N-[4-[2-[[2-hydroxy-3-(4-hydroxyphenoxy)propyl]amino]ethyl]-phenyl]-4-iodobenzenesulfonamide is used as a control in all assays. Isoproterenol is titrated at a final concentration in the assay of $10^{-10}$M to $10^{-5}$M for the β3 AR and $10^{-11}$M to $10^{-6}$M for the β1 AR and β2 AR assays. L-742,791 is titrated at the β3 receptor at concentration of $10^{-11}$M to $10^{-6}$M. At the β1 AR the concentrations used are $10^{-8}$M, $10^{-7}$M, $3\times10^{-7}$M, $10^{-6}$M, $3\times10^{-6}$M and $10^{-5}$M. For the β2 AR a single concentration of $10^{-5}$M is used.

Unknown ligands are initially tested at the β3 AR at a final concentration in the assay of $10^{-7}$M. Compounds that have an activation at this concentration equal to or greater than 35% of the isoproterenol stimulation are titrated at the β3 AR at concentrations equal to those used to titrate the control (S)-N-[4-[2-[[2-hydroxy-3-(4-hydroxyphenoxy)propyl]amino]ethyl]-phenyl]-4-iodobenzenesulfonamide to determine the $EC_{50}$. The $EC_{50}$ is defined as the concentration of compound that gives 50% activation of its own maximum. Data are analyzed using the Prism program (GraphPan, San Diego, Calif.).

A selective compound is defined as a compound with a $EC_{50}$ β3 AR)/($IC_{50}$ β1 AR, β2 AR) greater than 100. $IC_{50}$ is defined in the next section. Selective compounds are tested for agonist activity at the β1 AR and the β2 AR by assaying first at a single concentration, $10^{-5}$M. Compounds with activations of less than 20% when compared to the isoproterenol control (β3 AR and β2 AR) are retested at $10^{-7}$M and $10^{-5}$M. Compounds with activations between 20% and 40% and other compounds of interest are titrated at the following concentrations: $10^{-8}$M, $10^{-7}$M, $10^{-6}$M, $3\times10^{-6}$M, $10^{-5}$M and $3\times10^{-5}$M. Compounds with activities greater than 40% are not tested further.

Binding Assay: Compounds are also assayed at the β1 and β2 receptors to determine selectivity. This is done for all compounds using a 6 point binding assay as follows: CHO cells expressing the β1 and the β2 receptors are grown for 3–4 days after splitting. The attached cells are washed with PBS and lysed in 1 mM Tris, pH 7.2 for 10 minutes in ice. The flasks are scraped and the membranes centrifuged at 38,000×g for 15 minutes at 4° C. The membranes are resuspended in TME buffer (75 mM Tris, pH 7.4, 12.5 mM $MgCl_2$, 1.5 mM EDTA) at a concentration of 1 mg protein/ml. Large batches of membranes can be prepared, aliquoted and stored at −70° C. for up to a year without loss of potency. The binding assay is performed by incubating together membranes (20–50 μg of protein), the radiolabelled tracer $^{125}$I-cyanopindolol ($^{125}$I-CYP, 45 pM), and the test compounds at final concentrations ranging from $10^{-10}$M to $10^{-5}$M in a final volume of 250 μL of TME buffer. The tubes are incubated for 1 hour with shaking at room temperature and the samples are filtered in an IMSCO 96-well cell harvester. The filters are counted in a Gamma counter and the data are analyzed using a 4 parameter fit routine in RS1 (program developed in house using well documented statistical analysis programs) to determine the $IC_{50}$. The $IC_{50}$ is defined as the concentration of the compound capable of inhibiting 50% of the binding of the radiolabelled tracer ($^{125}$I-CYP). Compounds having >100 fold selectivity are also tested for agonist activity at the β1 and β2 receptors following the protocols already described for the β3 AR above.

The following examples are provided so that the invention might be more fully understood. They should not be construed as limiting the invention in any way.

EXAMPLE 1

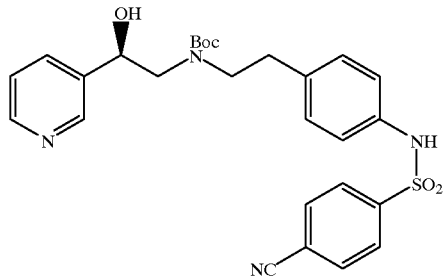

(R)-N-[4-2-[N-(1,1-Dimethylethoxycarbonyl)-N-[2-hydroxy-2-(pyridin-3-yl)ethyl]amino]ethyl]phenyl]-4-cyanobenzenesulfonamide To a solution of 2.18 mmol of (R)-N-[2-[4-(aminophenyl)]ethyl]-2-hydroxy-2-(pyrid-3-yl) ethylcarbamic acid 1,1-dimethylethyl ester (See Fisher, et. al., WO9529159-A, Nov. 2, 1995, for the synthesis of this compound.) in 10 mL of methylene chloride at room temperature was added 160 μL of pyridine followed by 450 mg of 4-cyanobenzenesulfonyl chloride. The resultant mixture was stirred overnight. TLC (acetone 25%, methylene chloride 75%) on silica indicated the formation of a major fast moving (rf 0.48) spot. Purification by flash chromatography gave 716 mg of the title compound as a white solid: $^1$H NMR (400 MHz, $CDCl_3$) d 8.53–8.44(m, 2H), 7.78 and 8.67 each (d, J=8.7 Hz, 2H), 7.3(m, 1H), 7.1–6.9(m, 4H), 4.8(m, 1H), 3.5–2.6(m, 6H), 1.42(s, 9H).

EXAMPLE 2

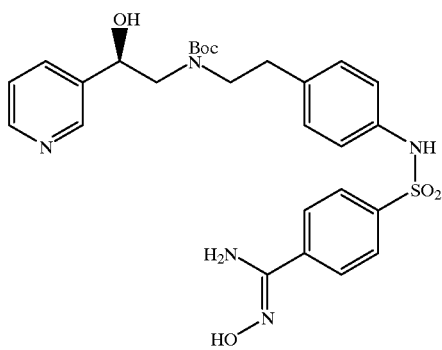

(R)-N-[4-[2-[N-(1,1-Dimethylethoxycarbonyl)-N-[2-hydroxy-2-(pyridin-3-yl)ethyl]amino]ethyl]phenyl]-4-(aminooximidomethyl)benzenesulfonamide Fifteen g of finely ground $K_2CO_3$ was suspended in 150 mL of absolute ethanol and after about 1 hr. 9 g of the nitrile from Example 1 and 6 g of hydroxylamine hydrochloride were added and stirred under reflux for 16 hr. The reaction mixture was cooled to room temperature and treated with 150 mL of methylene chloride and filtered through a bed of silica (30 g). The silica was washed with 200 mL of 20% methanol/methylene chloride, and the combined filtrate evaporated and dried under vacuum overnight to yield 9 g of the title compound as a white solid: $^1$H NMR (400 MHz, $CD_3OD$) δ 8.50–8.40(m, 2H), 7.93–7.67(m, 5H), 7.40(m, 1H), 7.08–6.96(m, 4H), 4.84(m, 1H), 3.4–2.6(m, 6H), 1.32 (s, 9H).

EXAMPLE 3

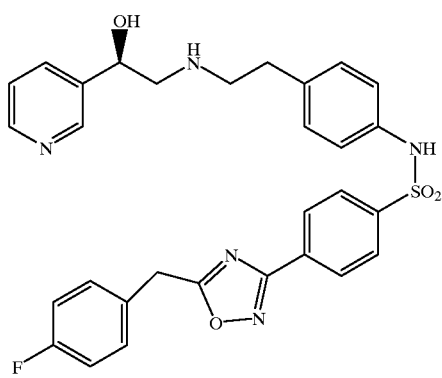

(R)-N-[4-[2-[[2-Hydroxy-2-(pyridin-3-yl)ethyl]amino]ethyl]phenyl]-4-[5-(4-fluorophenylmethyl)-[1,2,4]-oxadiazol-3-yl]benzenesulfonamide A suspension of 550 mg of the amidoxime from Example 2, 210 mg of EDC, and 160 mg of 4-fluorophenylacetic acid in 7 mL of diglyme was heated (oil bath temp. 110 degrees) while stirring. TLC analysis after 1 h indicated the formation of a new spot more mobile than the amidoxime (rf 0.61, methanol/methylene chloride 7/93). Following overnight heating, this converted to a new more mobile spot (rf 0.72). Purification by flash chromatography on silica and deprotection of the BOC group by treatment with 1:1 TFA/methylene chloride, neutralization with 10% ammonium hydroxide in methanol, and purification by flash chromatography (silica, aqueous ammonium hydroxide, methanol, dichloromethane 1/9/90) gave 305 mg of the title compound: $^1$H NMR (400 MHz, $CD_3OD$) δ 8.51(d, J=2.26 Hz, 1H), 8.42–8.40(m, 1H), 8.11(d, J=8.6 Hz, 2H), 7.82(d, J=8.6 Hz, 2H), 7.79(m, 1H), 7.4–7.37(m, 3H), 7.08 & 7.01(ea. d, J=8.5 Hz, ea. 2H), 7.01(m, 2H), 4.78(m, 1H), 4.33(s, 2H), 2.9–2.7 (m, 6H).

EXAMPLE 4

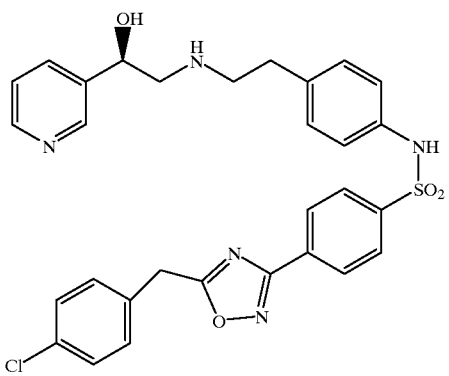

(R)-N-[4-[2-[[2-Hydroxy-2-(pyridin-3-yl)ethyl]amino]ethyl]phenyl]-4-[5-(4-chlorophenylmethyl)-[1,2,4]-oxadiazol-3-yl]benzenesulfonamide The title compound was prepared as described above for Example 3: $^1$H NMR (400 MHz, $CD_3OD$) δ 8.51(d, J=1.6 Hz, 1H), 8.42–8.40(m, 1H), 8.11(d, J=8.34 Hz, 2H), 7.82(d, J=8.34 Hz, 2H), 7.79(m, 1H), 7.4–7.3(m, 5H), 7.08 & 7.01(ea. d, J=8.35 Hz, ea. 2H), 4.78(m, 1H), 4.33(s, 2H), 2.9–2.7(m, 6H).

EXAMPLE 5

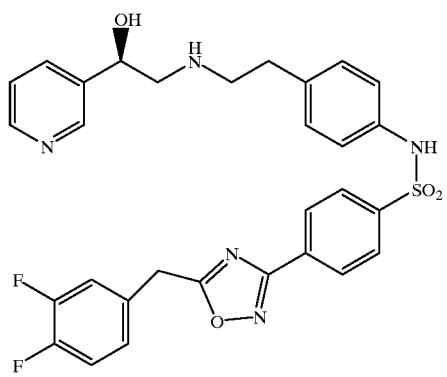

(R)-N-[4-[2-[[2-Hydroxy-2-(pyridin-3-yl)ethyl]amino]ethyl]phenyl]-4-[5-(3,4-difluorophenylmethyl)-[1,2,4]-oxadiazol-3-yl]benzenesulfonamide The title compound was prepared as described above for Example 3: $^1$H NMR (400 MHz, $CD_3OD$) δ 8.52(d, J=2.2 Hz, 1H), 8.42–8.40(m, 1H), 8.12(d, J=8.58 Hz, 2H), 7.83(d, J=8.58 Hz, 2H), 7.8(m, 1H), 7.4–7.14(m, 4H), 7.09 & 7.02(ea. d, J=8.5 Hz, ea. 2H), 4.78(m, 1H), 4.35(s, 2H), 2.9–2.7(m, 6H).

EXAMPLE 6

(R)-N-[4-[2-[[2-Hydroxy-2-(pyridin-3-yl)ethyl]
amino]ethyl]phenyl]-4-[5-(3,4-
difluorophenylmethyl)-[1,2,4]-oxadiazol-3-yl]
benzenesulfonamide dihydrochloride salt The free base prepared above in Example 5 (500 mg) was dissolved in 1.5 mL of methanol and treated with a solution that contains 210 μL of acetyl chloride in methanol and stirred at 0° C. for 30 min. Solvent was evaporated and the residue dried under vacuum overnight to give the dihydrochloride salt as a white solid: $^1$H NMR (400 MHz, CD$_3$OD) δ 8.97(d, J=1.2 Hz, 1H), 8.86(d, J=5.81, 1H), 8.70(d, J=8.07, 1H), 8.12(d, J=8.53 Hz, 2H), 8.1(m, 1H), 7.87(d, J=8.53 Hz, 2H), 7.4–7.2(m, 4H), 7.17 & 7.10(ea. d, J=8.58 Hz, ea. 2H), 5.3(m, 1H), 4.37(s, 2H), 2.9–3.5(m, 6H). EXAMPLE 7

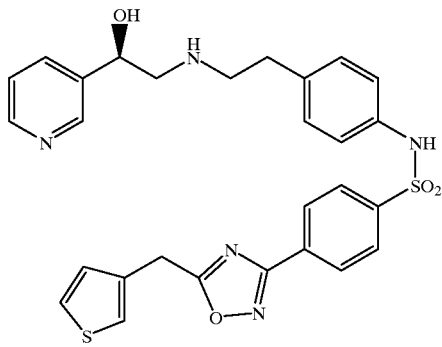

(R)-N-[4-[2-[[2-Hydroxy-2-(pyridin-2yl)ethyl]
amino]ethyl]phenyl]-4-[5-[(thiophen-3-yl)methyl]-
[1,2,4]-oxadiazol-3-yl]benzenesulfonamide The title compound was prepared as described above for Example 3: $^1$H NMR (400 MHz, CD$_3$OD, ppm) δ 2.70–2.90 (m, 6H), 4.37 (s, 2H), 4.83 (m, 1H), 7.0–7.1 (m, 5H), 7.3–7.4 (m, 3H), 7.82 (m, 3H), 8.13 (m, 2H), 8.42 (m, 1H), 8.51 (m, 1H).

EXAMPLE 8

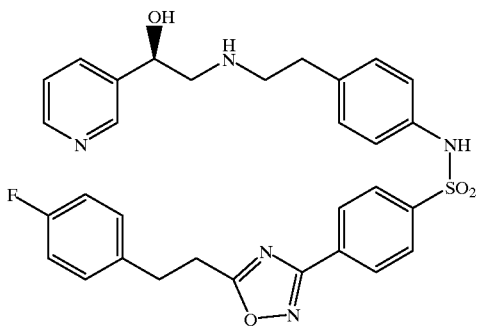

(R)-N-[4-[2-[[2-Hydroxy-2-(pyridin-3-yl)ethyl]
amino]ethyl]phenyl]-4-[5-[2-(4-fluorophenyl)ethyl]-
[1,2,4]-oxadiazol-3-yl]benzenesulfonamide The title compound was prepared as described above for Example 3: Selected $^1$H NMR Data (400 MHz, CD$_3$OD) δ 8.12(d, J=8.30 Hz, 2H), 7.83(d, J=8.48 Hz, 2H), 7.24(m, 2H), 6.97(m, 2H), 3.27(t, J=7.06 Hz, 2H), 3.15(t, J=7.24 Hz, 2H).

EXAMPLE 9

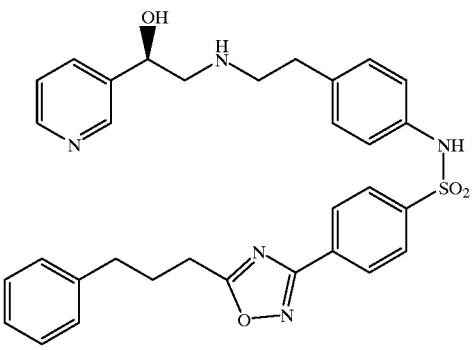

(R)-N-[4-[2-[[2-Hydroxy-2-(pyridin-3-yl)ethyl]
amino]ethyl]phenyl]-4-[5-(3-phenyl)propyl]-[1,2,4]-
oxadiazol-3-yl]benzenesulfonamide The title compound was prepared as described above for Example 3: Selected $^1$H NMR Data (400 MHz, CD$_3$OD) δ 8.10(d, J=8.62 Hz, 2H), 7.83(d, J=8.57 Hz, 2H), 7.24(m, 1H), 7.16(m, 4H), 2.94(t, J=7.52 Hz, 2H), 2.82(m, 2H), 2.14(qn, J=7.42 Hz, 2H).

EXAMPLE 10

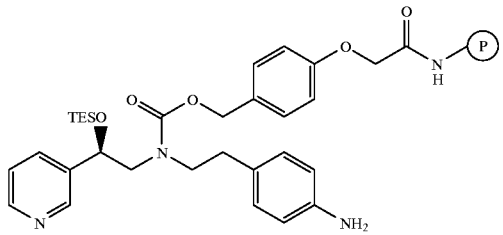

Step A: Preparation of the Resin-Bound Aniline

To 10 g of NovaSyn® TGA resin from Novabiochem in 30 mL of 1:1 tetrahydrofuran/dichloromethane (THF/DCM) was added 4 mL of diisopropylethylamine (DIEA) and 5 g of 4-nitrophenyl chloroformate. The resultant mixture was stirred overnight. The resin was thoroughly washed with THF/DCM until the eluate was colorless, treated with 2 mL of DIEA and 2 g of (R)-N-[2-[4-(aminophenyl)]ethyl]-2-hydroxy-2-(pyrid-3-yl)ethylamine (See Fisher, et. al., WO9529159-A, Nov. 2, 1995, for the synthesis of this compound.) in 20 mL of DMF, and allowed to stir overnight. The resin was washed with DMF, treated with 2 mL of DIEA, 2 mL of triethylsilyl chloride and 10 mL of DMF, and allowed to stir overnight. The resin was then washed successively with 20% aqueous DMF, DMF, THF, iPrOH, ACOH and dichloromethane.

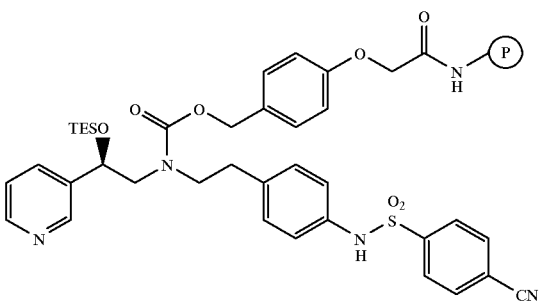

Step B: Preparation of the Resin-Bound Cyanobenzenesulfonamide

The above resin from Step A was treated with 3 mL of pyridine and 5 g of 4-cyanobenzenesulfonyl chloride in 30 mL dichloromethane and the reddish suspension was allowed to stir overnight. The resin was then washed successively with methanol, AcOH and dichloromethane and a small portion of the resin was cleaved with 1:1 dichloromethane/TFA and the purity was checked by HPLC.

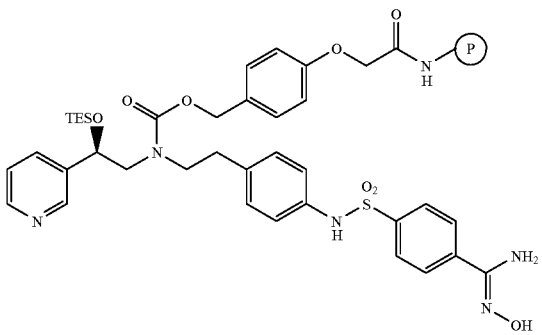

Step C: Preparation of the Resin-Bound Amidoxime

The resultant cyano compound from Step B was suspended in 50 mL ethanol and treated with 3.6 g of powdered potassium carbonate and 1.8 g of hydroxylamine hydrochloride and stirred at 75° C. for 16 hrs. A small portion was cleaved as above and checked by HPLC, which indicated the presence of the desired amidoxime and the corresponding amide in a 9:1 ratio. The resin was washed as above and used to prepare oxadiazoles as shown below.

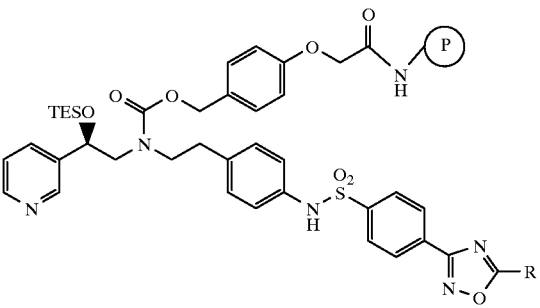

Step D. Preparation of Resin-Bound Oxadiazoles

A 100-mg portion of the amidoxime resin (0.025 mmole) from Step C and 1 mL diglyme was allowed to swell for 15 mnin with stirring, and the excess diglyme was drained to the level of the top of resin. To this was added a mixture of 0.25 mmol (10 equiv) of the desired carboxylic acid, 50 mg (0.25 mmol, 10 equiv) of EDC and 1.75 mL of diglyme which had previously been sonicated in a scintillation vial for 20 sec. The tube was covered with a Teflon cover, vented to release excess pressure, and heated on a rack at 99° C. After 5 minutes, it was vented again. Heating continued for 16 hrs. Diglyme was then drained and the resin was washed successively with DMF, THF/DCM, DCM, and AcOH and dried with a gentle nitrogen blow.

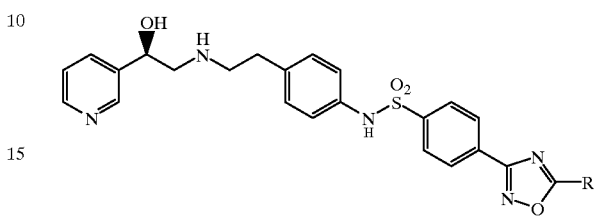

Step E. Oxadiazole Final Products

The resin was treated with 1:1 TFA-DCM for 5 minutes. The solvent was drained, and the procedure was repeated. The combined eluants were concentrated to dryness to give the desired oxadiazole as its bistrifluoroacetic acid salt.

Following the procedures outlined for Examples 1–10, the compounds listed in Table 1 were prepared.

TABLE 1

| Example | R | Selected $^1$HNMR (CD$_3$OD) Data |
|---|---|---|
| 11 | 3-fluorophenylmethyl, bistrifluoroacetate salt | 4.32(s, 2H), 5.22(m, 1H), 7.15–7.02(m, 6H), 7.38(m, 2H) |
| 12 | 3,4,5-trifluorophenylmethyl | 4.35(s, 2H), 4.78(m, 1H), 7.20 (m, 2H) |
| 13 | 3-chlorophenylmethyl, bistrifluoroacetate salt | 4.30(s, 2H), 5.20(m, 1H), 7.3–7.1(m, 3H) |
| 14 | 2-bromophenylmethyl, bistrifluoroacetate salt | 4.41(s, 2H), 5.38(m, 1H), 7.3–7.1(m, 2H), 7.61(d, 1H) |
| 15 | 4-methylphenylmethyl, bistrifluoroacetate salt | 2.28(s, 3H), 4.27(s, 2H), 5.20(m, 1H), 8.10 & 7.83 (ea d, ea 2H) |
| 16 | 2,4-difluorophenylmethyl, bistrifluoroacetate salt | 4.38(s, 2H), 5.21(m, 1H), 7.90(m, 2H), 7.5(m, 1H) |
| 17 | 3,5-difluorophenylmethyl, bistrifluoroacetate salt | 4.40(s, 2H), 7.85(m, 2H), 8.41(m, 1H) |
| 18 | 3-pyridylmethyl | 4.78(m, 1H), 7.36(m, 1H), 7.40(m, 1H), 7.90(m, 1H), 8.49(s, 1H) |
| 19 | 4-(2-pyridyl)phenylmethyl, bistrifluoroacetate salt | 4.50(s, 2H), 5.20(m, 1H), 8.78(m, 2H) |
| 20 | 4-(3-pyridyl)phenylmethyl, bistrifluoroacetate salt | 4.47(s, 2H), 5.18(m, 1H), 9.12(s, 1H) |
| 21 | 3,5-bis(trifluoromethyl)-phenylmethyl, bistrifluoroacetate salt | 4.60(s, 2H), 5.22(m, 1H), 7.92(s, 1H), 8.06(2, 2H) |

TABLE 1-continued

| Example | R | Selected ¹HNMR (CD₃OD) Data |
|---|---|---|
| 22 | 4-fluoro-3-(trifluoromethyl)phenylmethyl, bistrifluoroacetate salt | 4.46(s, 2H), 5.23(m, 1H), 7.33(t, 1H), 7.7(m, 1H), 7.76(d, 1H), 8.0(m, 1H) |
| 23 | 4-(trifluoromethyl)-phenylmethyl | 4.47(br s, 2H), 4.7(m, 1H), 8.12 & 7.8(ea d, ea 2H) |
| 24 | 4-(methylthio)phenylmethyl | d 2.44(s, 3H), 2.75–2.90(m, 6H), 4.29(s, 2H), 4.82(m, 1H), 7.01–7.10(m, 4H), 7.22–7.29(m, 4H), 7.40(m, 1H), 7.82(m, 3H), 8.11(m, 2H), 8.43(m, 1H) |
| 25 | 4-(methylsulfonyl)phenylmethyl | d 2.78–3.06(m, 6H), 3.12(s, 2H), 4.49(m, 1H), 7.02–7.15(m, 4H), 7.40–7.46(m, 1H), 7.64–7.68(m, 2H), 7.81–7.96(m, 5H), 8.12(m, 2H), 8.46(m, 1H), 8.56(m, 1H) |
| 26 | 3,4-methylenedioxyphenylmethyl | 4.26(s, 2H), 4.8(m, 1H), 5.92(s, 2H), 6.87(s, 1H), 6.78 & 6.83 (ea d, ea 1H) |
| 27 | 2-naphthylmethyl | 4.50(s, 2H), 4.88(m, 1H), 7.80(m, 6H), 7.38(m, 1H) |
| 28 | 3-indolylmethyl | 4.46(s, 2H), 4.78(m, 1H), 7.26(s, 1H), 7.32 & 7.53 (ea d, J=7.9 Hz, ea 1H) |
| 29 | 5-fluoroindol-3-ylmethyl | 4.42(s, 2H), 4.77(m, 1H), 7.3(s, 1H), 7.3 & 7.8 (ea m, ea 1H) |
| 30 | benzo[b]thien-3-ylmethyl | d 2.73–2.86(m, 6H), 4.62(s, 2H), 4.80(m, 1H), 7.00–7.09(m, 4H), 7.35–7.40(m, 3H), 7.57(s, 1H), 7.79–7.85(m, 4H), 7.88–7.90(m, 1H), 8.11(m, 2H), 8.40(m, 1H), 8.51(m, 1H) |
| 31 | 5-chlorobenzo[b]thien-3-ylmethyl | d 2.72–2.80(m, 6H), 4.59(s, 2H), 4.78(m, 1H), 7.00–7.08(m, 4H), 7.33–7.38(m, 2H), 7.67(m, 1H), 7.79–7.89(m, 5H), 8.10(m, 2H), 8.41(m, 1H), 8.51(m, 1H) |
| 32 | 2,3-dihydrobenzofur-5-ylmethyl, bistrifluoroacetate salt | 2.90(m, 2H), 4.23(s, 2H), 4.50(m, 2H), 5.2(m, 1H) |
| 33 | 2-(4-methoxyphenyl)ethyl | 8.11(d, J=8.62Hz, 2H), 7.83(d, J=8.62Hz, 2H), 7.13(d, J=8.62Hz, 2H), 6.81(d, J=8.71Hz, 2H), 3.72(s, 3H), 3.23(t, J=7.06Hz, 2H), 3.09(t, J=7.75Hz, 2H) |
| 34 | 2-phenylethyl | 8.11(d, J=8.53Hz, 2H), 7.83(d, J=8.62Hz, 2H), 7.23(m, 4H), 7.17(m, 1H), 3.27(t, J=7.70Hz, 2H), 3.16(t, J=7.47Hz, 2H) |
| 35 | 2-(4-chlorophenyl)ethyl | 8.11(d, J=8.57Hz, 2H), 7.83(d, J=8.57Hz, 2H), 7.26(d, J=8.72Hz, 2H), 7.22(d, J=8.67Hz, 2H), 3.27(t, J=7.05Hz, 2H), 3.15(t, J=7.47Hz, 2H) |
| 36 | 3-(4-methoxyphenyl)propyl | 8.11(d, J=8.57 Hz, 2H), 7.83 (d, J=8.53 Hz, 2H), 7.09(d, J=8.30 Hz, 2H), 6.79 (d, J=8.62 Hz, 2H), 3.69 (s, 3H), 2.93 (t, J=7.47 Hz, 2H), 2.66 (t, J=7.47 Hz, 2H), 2.12 (qn, J=7.33 Hz, 2H) |
| 37 | 2,5-difluorophenyl | 7.95(m, 1H), 7.80(m, 1H), 7.47(m, 1H) |
| 38 | 3,5-difluorophenyl | 7.8(m, 3H), 7.37(m, 2H) |
| 39 | 3-trifluoromethylphenyl | 8.47(s, 1H), 8.46 & 8.00(ea d, J=7.9Hz), ea 1H), 7.8(m, 1H) |
| 40 | 3-nitrophenyl | 8.99(t, J=1.76, 1H), 8.58(d, J=8.1, 1H), 8.54(dd, J=8.2, 1.3 Hz, 1H), 7.80(d, J=7.9Hz, 1H) |
| 41 | 3-methylthiophenyl | 2,53(s, 3H), 7.97(s, 1H), 7.94(d, J=7.88, 1H), 7.47(m, 2H) |
| 42 | 3-methylsulfonylphenyl | 3.21(s, 3H), 8.73(s, 1H), 8.51(1H), 8.41(m, 1H), 7.82(d, 1H) |
| 43 | 2-methylphenyl | 8.11(d, J=7.9, 1H), 7.53(m 1H), 7.41(m, 3H), 2.73(s, 3H) |
| 44 | 3-methylphenyl | 8.0(s, 1H), 7.96(d, 1H), 7.47(s, 2H), 2.42(s, 3H) |
| 45 | 3-methoxyphenyl | 7.76(d, J=8.1H, 1H), 7.69(m, 1H), 7.51(t, J=8.1, 1H), 7.23(m, 1H), 3.89(3, 3H) |
| 46 | 3-pyridyl | 9.33(s, 1H), 8.82(dd, J=6.5, 1.6, 1H), 7.67(m, 1H) |
| 47 | 2,3-dimethoxyphenyl | 7.62(dd, J=7.8, 1.6 Hz, 1H)), 7.32(dd, J=8.2, 1.6, 1H), 7.25(t, J=7.9), 3.94 & 3.96(s, ea 3H) |
| 48 | 2-benzofuranyl | 7.88(s, 1H), 7.81(m, 2H), 7.54(m, 1H), 7.38(m, 2H) |
| 49 | 5-fluoro-2-indolyl | 7.8(m, 2H), 7.35(m, 3H), 7.05(m, 5H) |
| 50 | biphen-4-ylmethyl, bistrifluoroacetate salt | 7.77(m, 3H), 7.53(m, 4H), 7.4(m, 4H), 4.38(s, 2H) |
| 51 | 5-methylisoxazol-3-yl | 2.57(s, 3H) |
| 52 | 4-fluorophenyl | 8.25(m, 2H), 7.35(t, J=8.7 Hz, 2H) |
| 53 | 3-fluorophenyl | 8.02(m, 1H), 7.9(m, 1H), 7.65(m, 1H), 7.42(m, 1H) |
| 54 | 4-fluorophenylcarbonyl | 8.56(m, 1H), 7.81(m, 1H), 7.34(m, 1H), 7.05(m, 1H) |
| 55 | 4-chlorophenylcarbonyl | 8.44(br, m, 1H), 7.80(br, m, 1H), 7.38(br, m, 1H), 7.03(br, m, 1H) |
| 56 | 3-(4-fluorophenyl)-3-oxopropyl | 8.09(m, 2H), 7.23(m, 2H), 3.67(t, J=6.68Hz, 2H), 3.34(t, J=7.05Hz, 2H) |
| 57 | 2-(3,4-difluorophenyl)ethyl | 7.15(m, 2H), 7.03(m, 1H), 3.27(t, J=7.14Hz, 2H), 3.15(t, J=7.47Hz, 2H) |
| 58 | 2-naphthyloxymethyl | 7.77(m, 3H), 7.38(m, 4H), 5.57(s, 2H) |
| 59 | 4-fluorophenoxymethyl | 7.05(m, 8H), 5.42(s, 2H) |
| 60 | 3-acetamidophenoxymethyl, bistrifluoroacetate salt | 8.5(m, 1H), 7.94(m, 1H), 7.81(m, 1H), 7.2(m, 1H), 5.42(s, 2H), 2.10(s, 3H) |
| 61 | 3-trifluoromethylphenoxymethyl, bistrifluoroacetate salt | 8.42(m, 1H), 7.5(m, 1H), 5.55(s, 2H) |
| 62 | 4-(acetyloxy)-phenoxymethyl, bistrifluoroacetate salt | 8.5(d, 1H), 7.9(m, 1H), 7.8(m, 1H), 5.56(s, 2H), 2.52(s, 3H) |
| 63 | 4-methylphenoxymethyl, bistrifluoroacetate salt | 7.13 & 6.90(ea d, ea 2H), 5.38(s, 2H), 2.23(s, 3H) |

TABLE 1-continued

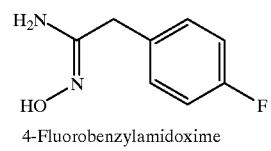

| Example | R | Selected ¹HNMR (CD₃OD) Data |
|---|---|---|
| 64 | 2-phenoxyethyl | 7.24(t, J=7.42Hz, 2H), 6.91(m, 3H), 4.46(t, J=6.17Hz, 2H), 3.45(t, J=6.13 Hz, 2H) |
| 65 | 3,4-difluorophenoxymethyl, bistrifluoroacetate salt | 8.46(d, J=7 Hz), 7.93(m, 1H), 7.20(m, 1H), 5.20(m, 1H), 5.46(s, 2H) |

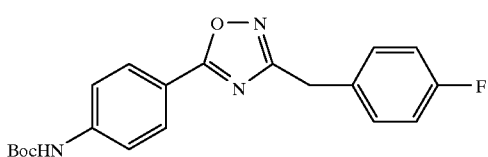

4-Fluorobenzylamidoxime

To a stirred suspension of hydroxyamine hydrochloride (1.5 g, 3 equiv) and potassium carbonate (4.0 g, 4 equiv) in ~95% aqueous EtOH (15 mL) was added 4-fluorophenylacetonitrile (1.0 g, 7.4 mmol) in one portion. The resulting mixture was stirred at reflux overnight. The reaction was quenched with water, and the aqueous mixture was extracted with EtOAc (3×). The combined organic solution was washed with water and brine, dried with Na₂SO₄, and evaporated. The yellow oil residue was purified by flash column chromatography on silica gel, and eluted with 80–90% EtOAc in hexane. The product (300 mg) was isolated as off-white crystalline solid: ¹H NMR (400 MHz, CDCl₃) δ 3.41 (s, 2H), 4.48 (broad, 2H), 6.98 (m, 2H), 7.21 (m, 2H), 8.8 (very broad, 1H).

EXAMPLE 67

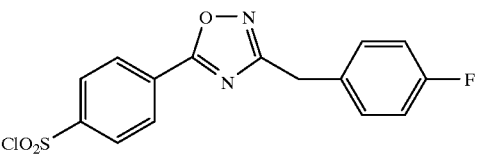

3-(4-Fluorobenzyl)-5-(4-N-tBoc-aminophenyl)-1,2,4-oxadiazole

To a stirred solution of 4-N-tBoc-aminobenzoic acid (425 mg, 1 equiv) in diglyme (3 mL) was added 4-fluorobenzylamidoxime (300 mg, 1.8 mmol) followed by EDC (350 mg, 1 equiv). The reaction was stirred at room temperature overnight, and then heated to 100° C. for 3 hr under nitrogen. After cooling, solvent was evaporated and the residue was purified by flash column chromatography on silica gel, and eluted with 1–2% methanol in dichloromethane. The product (150 mg) was isolated as viscous yellow oil: ¹H NMR (400 MHz, CDCl₃) δ 1.50 (s, 9H), 4.06 (s, 2H), 7.0 (m, 2H), 7.3 (m, 2H), 7.48 (d, J=8.8 Hz, 2H), 8.00 (d, J=8.8 Hz, 2H).

EXAMPLE 68

3-(4-Fluorobenzyl)-5-(4-chlorosulfonylphenyl)-1,2,4-oxadiazole

To a stirred solution of the above oxadiazole from Example 67 (150 mg, 0.4 mmol) in dichloromethane (2.5 mL) was added TFA (2.5 mL) in one portion. After 2 hr, solvent and TFA were evaporated under a stream of nitrogen. The solid residue was taken up into concentrated hydrochloric acid (4 mL) and glacial acetic acid (1 mL) with stirring. The resulting mixture was cooled to −10° C., and a solution NaNO₂ (50 mg, 2 equiv) in water (1 mL) was added dropwise so that the reaction temperature was lower than −5° C. After the addition, the orange colored mixture was stirred for 45 min, and then transferred onto a saturated solution of SO₂ in glacial AcOH (~4 mL) containing CuCl (100 mg) at 0–10° C. The resulting olive-green mixture foamed during the addition, and slowly turned yellow. After 40 min. at room temperature, the reaction was poured onto ice-water, and extracted with EtOAc (3×). The combined organic solution was washed with cold water, cold aqueous NaHCO₃, and brine, dried with MgSO₄, and evaporated. The residue was purified by flash column chromatography on silica gel, and eluted with 25% EtOAc in hexane. The product (2.5 mg) was isolated as white solid: ¹H NMR (400 MHz, CDCl₃) δ 4.13 (s, 2H), 7.0 (m, 2H), 7.3 (m, 2H), 8.17 (d, J=8.8 Hz, 2H), 8.34 (d, J=8.8 Hz, 2H).

EXAMPLE 69

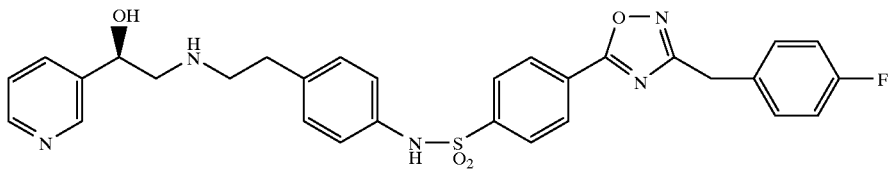

(R)-N-[4-[2-[[2-Hydroxy-2-(pyridin-2-yl)ethyl]amino]ethyl]phenyl]-4-[3-(4-fluorobenzyl)-[1,2,4]-oxadiazol-5-yl]benzensulfonamide To a stirred solution of the above sulfonyl chloride from Example 68 (2.5 mg, 0.007 mmol) in dichloromethane (1 mL) was added (R)-N-[2-[4-(aminophenyl)]ethyl]-2-hydroxy-2-(pyrid-3-yl)ethylcarbamic acid 1,1-dimethylethyl ester (3.6 mg, 1.4 equiv) and pyridine (1 drop). The reaction was stirred at room temperature overnight. After removing the solvent under reduced pressure, the residue was purified by flash column chromatography on silica gel, and eluted with EtOAc. The tBoc protecting group was then removed by stirring a dichloromethane solution (1 mL) of the compound with TFA (1 mL) at room temperature for 2 hr. Solvent and TFA were removed by a stream of nitrogen, and the residue was purified by flash column chromatography on silica gel, and eluted with 10% methanol (containing 1/10 aqueous ammonium hydroxide) in dichloromethane. The product (2 mg) was isolated as white solid: $^1$H NMR (400 MHz, CD$_3$OD) δ 2.70–2.90 (m, 6H), 4.12 (s, 2H), 4.82 (m, 1H), 7.05 (m, 6H), 7.3–7.4 (m, 3H), 7.82 (m, 1H), 7.88 (d, J=8.6 Hz, 2H), 8.18 (d, J=8.6 Hz, 2H), 8.42 (m, 1H), 8.52 (m, 1H).

EXAMPLE 70

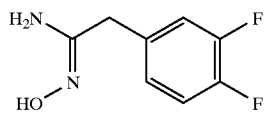

3,4-Difluorobenzylamidoxime

Following the procedure outlined in Example 66, the title compound was prepared: $^1$H NMR (400 MHz, CDCl$_3$) δ 3.39 (s, 2H), 4.46 (broad, 2H), 7.0 (m, 1H), 7.1 (m, 2H), 7.4 (very broad, 1H).

EXAMPLE 71

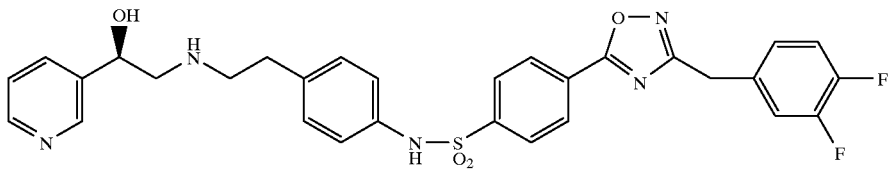

(R)-N-[4-[2-[[2-Hydroxy-2-(pyridin-2-yl)ethyl]amino]ethyl]phenyl]-4-[3-(3,4-difluorobenzyl)-[1,2,4]-oxadiazol-5-yl]benzensulfonamide To a stirred solution of (R)-N-[2-[4-(aminophenyl)]ethyl]-2-hydroxy-2-(pyrid-3-yl)ethylcarbamic acid 1,1-dimethylethyl ester (500 mg, 1.4 mmol) and pyridine (0.15 mL, 2 equiv) in diglyme (10 mL) was added 4-chlorosulfonyl benzoic acid (310 mg, 1 equiv). The orange red reaction mixture was stirred at room temperature overnight. To this mixture was added the above amidoxime from Example 70 (280 mg, 1.1 equiv) followed by DCC (310 mg, 1.1 equiv), and stirring was continued at room temperature for another day. The reaction was then heated to 100° C. for 3 hr. After removing the solvent in vacuo, the residue was purified by flash column chromatography on silica gel, and eluted with EtOAc. The tBoc protecting group was then removed by stirring a dichloromethane solution (2.5 mL) of the compound with TFA (2.5 mL) at room temperature for 2 hr. Solvent and TFA were removed by a stream of nitrogen, and the crude product was purified by flash column chromatography on silica gel, and eluted with 10% methanol (containing 1/10 aqueous ammonium hydroxide) in dichloromethane. The product (180 mg) was isolated as light yellow solid: $^1$H NMR (400 MHz, CD$_3$OD) δ 2.70–2.90 (m, 6H), 4.13 (s, 2H), 4.8 (m, 1H), 7.0–7.4 (m, 8H), 7.8 (m, 1H), 7.88 (d, J=8.6 Hz, 2H), 8.18 (d, J=8.6 Hz, 2H), 8.42 (m, 1H), 8.51 (m, 1H).

EXAMPLE 72

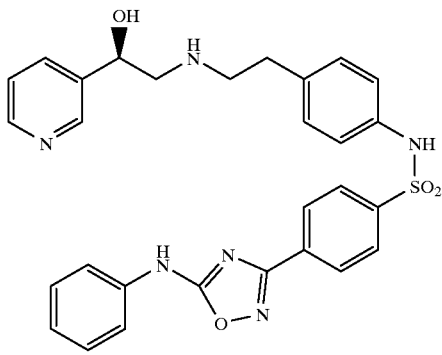

(R)-N-[4-[2-[[2-Hydroxy-2-(pyridin-3-yl)ethyl]amino]ethyl]phenyl]-4-(5-phenylamino-[1,2,4]-oxadiazol-3-yl)benzenesulfonamide To a solution of the amidoxime from Example 2 (100 mg, 0.18 mmol) and 1,8-diazabicyclo[5.4.0]undec-7-ene (DBU) (30 mg, 0.20 mmol) in anhydrous dichloromethane (20 ml) under nitrogen at 0° C., phenylisocyanide dichloride (31 mg, 0.18 mmol) was added slowly. The resulting solution was allowed to stir at 0° C. for 30 min. and then warm to room temperature and stir overnight. The crude product was purified by silica gel prep TLC(8% methanol/dichloromethane, containing 1% aqueous ammonium hydroxide). The resultant Boc derivative was treated with 50% trifluoroacetic acid in dichloromethane and then concentrated. The product was purified by silica gel prep TLC (12% methanol/dichloromethane, containing 1% aqueous ammonium hydroxide) to provide 19.0 mg (19%) of the title product: $^1$H NMR (CD$_3$OD) δ 8.54 (d, J=1.75 Hz, 1H), 8.43 (dd, J=4.98, 1.34 Hz, 1H), 8.13 (d, J=8.44 Hz, 2H), 7.84 (d, J=8.43 Hz, 2H), 7.83 (m, 1H), 7.63 (d, J=7.61 Hz, 2H), 7.40 (m, 1H), 7.36 (t, J=6.74 Hz, 2H), 7.12 (d, J=8.58 Hz, 2H), 7.09 (m, 1H), 7.06 (d, J=8.53 Hz, 2H), 4.84 (m, 1H), 2.93 (m, 4H), 2.81 (t, J=7.47 Hz, 2H).

EXAMPLE 73

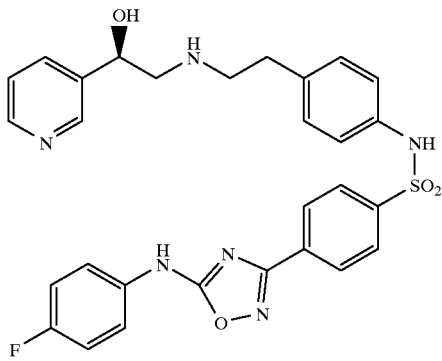

(R)-N-[4-[2-[[2-Hydroxy-2-(pyridin-3-yl)ethyl]amino]ethyl]phenyl]-4-[5-(4-fluorophenyl)amino-[1,2,4]-oxadiazol-3-yl]benzenesulfonamide Following the procedure outlined in Example 72, the title compound was prepared: Selected $^1$H NMR Data (CD$_3$OD) δ7.63(m, 2H), 7.10(m, 2H).

EXAMPLE 74

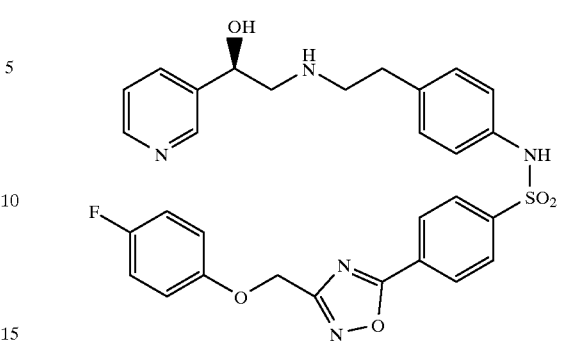

(R)-N-[4-[2-[[2-Hydroxy-2-(pyridin-3-yl)ethyl]amino]ethyl]phenyl]-4-[3-(4-fluorophenoxymethyl)-[1,2,4]-oxadiazol-5-yl]benzenesulfonamide Following the procedures outlined in Examples 70–71, the title compound was prepared: Selected $^1$H NMR Data (CD$_3$OD) δ 8.51 (m, 1H), 8.41 (m, 1H), 8.24 (d, J=8.6 Hz, 2H), 7.91 (d, J=8.6 Hz, 2H), 7.81 (m, 1H), 7.09 (d, J=8.53, 2H), 7.06–7.00 (m, 6H), 5.25 (s, 2H).

Following the procedures outlined for Examples 1–10, the compounds listed in Table 2 were prepared.

TABLE 2

| Example | R | Selected $^1$H NMR (CD$_3$OD) Data |
|---|---|---|
| 75 | 4-trifluoromethoxyphenoxymethyl, bistrifluoroacetate salt | 8.08 (m, 2H), 7.22 (d, 2H), 5.27 (m, 2H), 5.49 (s, 2H) |
| 76 | 4-trifluoromethoxyphenylmethyl, bistrifluoroacetate salt | 8.05 (m, 2H), 7.48 (d, 2H), 5.28 (m, 2H), 4.40 (s, 2H) |

EXAMPLE 77

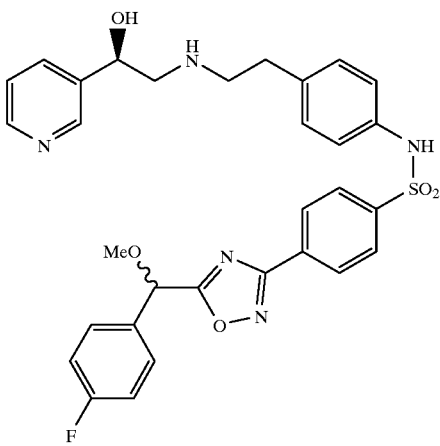

(R)-N-[4-[2-[[2-Hydroxy-2-(pyridin-3-5 yl)ethyl]
amino]ethyl]phenyl]-4-[5-[1-(4-fluorophenyl)-1-
methoxymethyl]-[1,2,4]-oxadiazol-3-yl]
benzenesulfonamide Step A. Methyl 4-Fluoromandelate 4-Fluoromandelic acid (2.53 g) in 10 ml of THF was treated with excess diazomethane etherate (generated from N-methyl-N-nitrosourea and aqueous potassium hydroxide at 0° C.). The reaction mixture was concentrated in vacuo, and the residue was partitioned between ethyl acetate and saturated aqueous sodium bicarbonate. The title compound (2.70 g) was isolated as an oil after drying and evaporation: Selected $^1$H NMR (400 MHz, CDCl$_3$) δ 3.08 (s, 3H) and 3.75 (s, 3H).

Step B. Methyl (4-Fluorophenyl)methoxyacetate

Sodium hydride (585 mg, 60% oil dispersion) was added in portions to a stirred solution of 2.02 g methyl 4-fluoromandelate obtained above in a mixture of 18 mL of THF and 3 mL of DMF at 0° C. After 10 min, iodomethane (1.95 mL, 3 equiv) was added and the mixture was allowed to warm up to room temperature and stir for 0.5 h. After evaporation and extraction with ethyl acetate, the organic phase was washed with water and brine, dried over magnesium sulfate, and the residue obtained after filtration and evaporation was purified by flash chromatography on silica column (20% ethyl acetate/hexane), affording 1.01 g of the title compound: $^1$H NMR (400 MHz, CDCl$_3$) δ 7.43–7.37 (m, 2H), 7.08–7.0 (m, 2H), 4.73 (s, 1H), 3.78 (s, 3H), 3.70 (s, 3H).

Step C. (4-Fluorophenyl)methoxyacetic acid

The above methyl ether methyl ester (1.01 g) and 3.67 mL of 2N aqueous sodium hydroxide in 14 mL of methanol at 0° C. was stirred at room temperature for 2 h. The mixture was evaporated, chilled in ice, acidified with 2N aqueous hydrochloric acid, extracted with ethyl acetate, washed with water and brine, and dried with magnesium sulfate. Evaporation yielded the corresponding carboxylic acid (1.0 g): Selected $^1$H NMR (400 MHz, CDCl$_3$) δ 3.70 (s, 3H).

Step D. (R)-N-[4-[2-[N-(1,1-Dimethylethoxycarbonyl)-N-[2-hydroxy-2-(pyridin-3-yl)ethyl]amino]ethyl]phenyl]-4-[5-[1-(4-fluorophenyl)-1-methoxymethyl]-[1,2,4]-oxadiazol-3-yl]benzenesulfonamide To a stirred mixture of equimolar molar quantities of the carboxylic acid from Step C (438 mg, 2.38 mmol) and the amidoxime from Example 2 (1.32 g, 2.38 mmol) in 14.3 mL of THF at room temperature under nitrogen was added EDC (456 mg, 2.38 mmol) in portions. The resultant mixture was stirred at ambient temperature for 16 h, and then heated at 50° C. for 1.5 h. The solvent (THF) was removed by evaporation and replaced with an equal volume of dry pyridine. The mixture was refluxed for 5 h, evaporated to an oil and purified by preparative TLC (SiO$_2$ plates) in 90:9:1 dichloromethane: methanol:aqueous ammonium hydroxide to give 881 mg of the title compound: $^1$H NMR (400 MHz, CDCl$_3$) δ 8.48 (br s, 2H), 8.11 (d, J=8.45 Hz, 2H), 7.79 (d, J=8.45 Hz, 2H), 7.69 (br s, 1H), 7.51–74.7 (m, 2H), 7.3–7.25 (m, 1H), 7.11–7.02 (m, 2H), 6.96 (br s, 4H), 5.57 (s, 1H), 4.89–4.82 (br s, 1H), 4.63–4.55 (br s, 1H), 3.47 (s, 3H), 3.44–3.06 (m, 4H), 2.83–2.57 (m, 3H), 1.41 (s, 9H).

Step E. (R)-N-[4-[2-[[2-hydroxy-2-(pyridin-3-yl)ethyl]amino]ethyl]phenyl]-4-[5-[1-(4-fluorophenyl)-1-methoxymethyl]-[1,2,4]-oxadiazol-3-yl]benzenesulfonamide The above N-Boc compound from Step D was deprotected with 24 mL of trifluoroacetic acid in 36 mnL of dichloromethane at 0° C. and at ambient temperature overnight. The mixture was evaporated and treated with 1 mL of 10% aqueous ammonium hyroxide in methanol and then the final residue obtained after evaporation was purified by preparative TLC (90:9:1 dichloromethane:methanol:aqueous ammonium hydroxide) to give 670 mg of the title compound: $^1$H NMR(400 MHz, CDCl$_3$) δ 8.51 (br s, 1H), 8.47–8.46 (m, 1H), 8.09 (d, J=8.49 Hz, 2H), 7.80 (d, J=8.49 Hz, 2H), 7.65 (m, 1H), 7.5–7.42 (m, 2H), 7.28–7.20 (m, 1H), 7.10–6.93 (m, 6H), 5.56 & 5.54 (2s, 1H), 5.02 (m, J=6.37 Hz, 1H), 4.8–4.65 (m, 1H), 3.45 & 3.44 (2s, 3H), 3.35–3.26 (m, 2H), 2.9–2.75 (m, 2H), 2.75–2.55 (m, 4H).

Following the procedures outlined for Examples 1–10 and 77, the compounds listed in Table 3 were prepared.

TABLE 3

| Example | R | Selected $^1$H NMR Data |
|---|---|---|
| 78 | 1-(3,4-difluorophenyl)-1-methoxymethyl | CDCl$_3$, 7.04(d, J=8.46Hz, 2H), 6.96(d, J=8.46Hz, 2H), 6.83(br s, 1H), 5.54(s, 1H), 3.48(s, 3H) |
| 79 | 1-(4-fluorophenyl)-1-ethoxymethyl | CDCl$_3$, 7.10–7.00(m, 4H), 7.00–6.92(m, 2H), 5.67(s, 1H), 3.61(q, J=13.56, 6.64Hz, 2H), 1.28(t, J=6.98Hz, 3H) |
| 80 | 1-(4-chlorophenyl)-1-methoxymethyl | CDCl$_3$, 7.09–6.91(m, 4H), 5.60(s, 1H), 3.46(s, 3H) |
| 81 | 1-(4-chlorophenyl)-1-ethoxymethyl | CDCl$_3$, 7.09–6.91(m, 4H), 5.66(s, 1H), 3.61(q,J=13.56, 6.64Hz, 2H), 1.29(t,J=6.98Hz, 3H) |
| 82 | 2-naphthyl | CDC$_3$OD/CDCl$_3$, 8.74(s, 1H), 1.7Hz, 1H), 8.73(d, J=1.8Hz, 8.16(dd, J=8.6, 1.7Hz, 1H), 8.02(d, J=8.4Hz, 2H), 7.93(d, J=7.9Hz, 1H), 7.61(m,2H) |
| 83 | 6-quinolinyl | CD$_3$OD/CDC l$_3$, 8.95(dd, J=4.3, 1.7Hz, 1H), 8.73(d, J=1.8Hz, |

TABLE 3-continued

[Structure shown: pyridinyl-CH(OH)-CH2-NH-CH2CH2-phenyl-NH-SO2-phenyl-oxadiazole-R]

| Example | R | Selected $^1$H NMR Data |
|---|---|---|
| | | 1H), 8.36(m,2H), 8.20(m, 1H), 7.55(dd, J=8.4, 4.3Hz,1H) |
| 84 | 3-methoxyphenoxymethyl | CD$_3$OD, 7.19(m,1H), 6.60(m, 3H), 5.41(s,2H), 3.75(s, 3H) |
| 85 | 3-chlorophenoxymethoxy | CD$_3$OD, 7.29(m, 1H), 7.04(m, 3H), 5.47(s, 2H) |
| 86 | 4-isopropylphenoxymethyl | CDCl$_3$, 7.15(dd, J=6.6, 2.1Hz, 2H), 6.91(m, 2H), 5.28(s, 2H), 2.90(m, 1H), 1.19(s, J=7.0Hz, 6H) |
| 87 | 4-chlorophenoxymethyl | CD$_3$OD/CDCl$_3$, 7.26(d, J=8.8Hz, 2H), 7.00(m, 2H), 5.40(s, 2H) |
| 88 | 3,4-dichlorophenoxymethyl | CD$_3$OD/CDCl$_3$, 7.42(d, J=9.0Hz, 1H), 7.25(d, J=3.0Hz, 1H), 7.00(m, 1H), 5.45(s, 2H) |
| 89 | 4-tert-butylphenoxymethyl | CD$_3$OD, 7.33(d, J=9.0Hz, 2H), 6.95(d,J=9.0Hz, 2H), 5.40(s, 2H), 1.27(s,9H) |
| 90 | 4-sulfonamidophenoxy-methyl | CD$_3$OD, 7.85(m, 2H), 7.19(d,J=9.0Hz, 2H), 5.56(s,2H) |
| 91 | 3-chloronaphth-1-yloxymethyl | CD$_3$OD, 8.21(d, J =8.3Hz, 1H), 7.75(m, 1H), 7.50(m, 3H), 7.10(m, 1H), 5.66(s, 2H) |
| 92 | 5-indanyloxymethyl | CD$_3$OD, 7.10(m, 1H), 6.89(s, 1H), 6.79(m,1H), 5.38(s,2H), 2.92–2.68(m, 10H), 2.04(quin, J=7.4Hz, 2H) |
| 93 | 4-indanyloxymethyl | CD$_3$OD, 7.05(m,1H), 6.87(d, J=7.5Hz, 1H), 6.78(d, J=8.0Hz, 1H), 5.43(s, 2H), 2.95–2.68(m, 10H), 2.05(quin, J=7.5Hz, 2H) |
| 94 | 2-chlorophenoxymethyl | CD$_3$OD, 7.39(m, 2H), 7.25(m, 1H), 7.19(dd, J=8.2, 1.1Hz 1H), 6.99(m, 1H), 5.52(s, 2H) |
| 95 | 3,5-dichlorophenoxymethyl | CD$_3$OD/CDCl$_3$, 7.10–6.98(m, 7H), 5.46(s, 2H) |
| 96 | 3-trifluoromethoxyphen-oxymethyl | CD$_3$OD, 7.39(m, 2H), 7.12–7.00 (m, 6H), 6.94(m, 1H), 5.50(s, 2H) |
| 97 | 4-(1,2-benzisoxazol-3-yl)-2,3-dichlorophenoxymethyl | CD$_3$OD/CDCl$_3$, 7.70–7.58(m, 3H), 7.51(d, J=8.7Hz, 1H), 7.40–7.28(m, 3H), 5.63(s, 2H) |
| 98 | 2,4-dichlorophenoxymethyl | CD$_3$OD, 7.47(d, J=2.6Hz, 1H), 7.29(dd, J=8.9, 2.6Hz, 1H), 7.21 (d, J=8.9Hz, 1H), 5.54(s, 2H) |
| 99 | 4-(2-quinazolinyl)phenoxym ethyl | CD$_3$OD/CDCl$_3$, 9.26(s, 1H), 8.18(d, J=8.6Hz, 2H), 8.10(dd, J=8.4, 1.4Hz, 1H), 8.05(dd, J=8.2, 1.4Hz, 1H), 7.82–7.70(m, 3H), 7.23(d, J=9.0Hz, 2H), 5.51(s, 2H) |
| 100 | 2,4,5-trichlorophenoxymethyl | CD$_3$OD/CDCl$_3$, 7.66(s, 1H), 7.37(s, 1H), 5.50(s, 2H) |
| 101 | 2,3-dichlorophenoxymethyl | CD$_3$OD, 7.29–7.13(m, 3H), 5.56(s, 2H) |
| 102 | 2-chloro-4-tert-butylphenoxymethyl | CD$_3$OD, 7.41(d, J=2.4Hz, 1H), 7.28(dd, J=8.6, 2.4Hz, 1H), 7.10 (m, 1H), 5.47(s, 2H), 1.27(s, 9H) |

TABLE 3-continued

[Structure shown: pyridinyl-CH(OH)-CH2-NH-CH2CH2-phenyl-NH-SO2-phenyl-oxadiazole-R]

| Example | R | Selected $^1$H NMR Data |
|---|---|---|
| 103 | 2,3-dichloro-4-(2-thienylsulfonyl)phenox ymethyl | CD$_3$OD, 8.24(d, J=9.1Hz, 1H), 7.91(dd, J=5.0, 1.4Hz, 1H, 7.89–7.78(m, 4H), 7.43(d, J=9.2Hz, 1H), 7.17(dd, J=4.9, 3.8Hz, 1H), 5.71(s, 2H) |
| 104 | 4-(N,N-dipropylsulfamoyl)phen oxymethyl | CD$_3$OD, 7.78(d, J=8.9Hz, 2H), 7.22(d, J=8.9Hz, 2H), 5.57(s, 2H), 3.04(m, 4H), 1.52(hextet, J=7.5Hz, 4H), 0.85(t, J=7.4Hz, 6H) |
| 105 | 4-trifluoromethylphenyl, bistrifluoroacetate salt | CD$_3$OD, 8.41(d, J=8.0Hz, 2H). 8.00–7.85(m, 5H) |
| 106 | 4-trifluoromethoxyphenyl | CD$_3$OD, 8.32(d, J=8.9Hz, 2H), 7.53(d, J=8.0Hz, 2H) |
| 107 | 3,4,5-trifluorophenyl | CD$_3$OD, 8.01(t, J=6.8Hz, 2H) |
| 108 | 6-fluoronaphth-2-yloxymethyl, bistrifluoroacetate salt | CD$_3$OD, 7.90(m, 1H), 7.79(d, J=9.1Hz, 1H), 7.50–7.40(m, 2H), 7.32–7.21(m, 2H), 5.57(s, 2H) |
| 109 | 6-fluoronaphth-2-ylmethyl | CD$_3$OD, 7.90–7.75(m, 6H), 7.50 (m, 2H), 7.28(m, 1H), 4.49(s, 2H) |

EXAMPLE 110

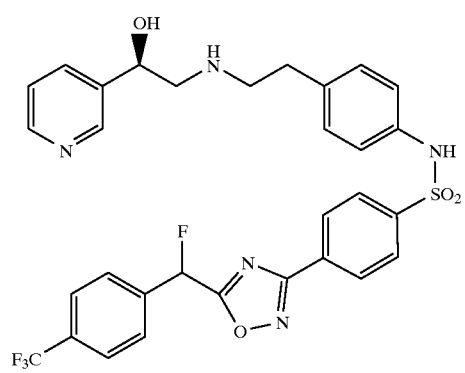

(R)-N-[4-[2-[[2-Hydroxy-2-(pyridin-3-yl)ethyl] amino]ethyl]phenyl]-4-[5-[1-fluoro-1-(4-trifluoromethylphenyl)methyl]-[1,2,4]-oxadiazol-3-yl]benzenesulfonamide Step A. Methyl 4-trifluoromethylphenylacetate A colorless solution of 4-trifluorophenylacetic acid (2.00 g, 9.8 mmol) in methanol (5 mL) containing concentrated H$_2$SO$_4$ (0.5 mL) was heated at reflux for 3 h. After cooling to RT, the volume of methanol was reduced in vacuo. Ice was added and the mixture extracted with diethyl ether (3×). The combined organic phase was washed with water, saturated NaHCO$_3$ solution (4×), water, brine, dried (MgSO$_4$)

and the solvent removed in vacuo to leave 1.98 g (93%) of the title compound as a colorless liquid: $^1$H NMR (300 MHz, CDCl$_3$) δ 7.58 (d, J=8.0 Hz, 2H), 7.40 (d, J=8.0 Hz, 2H), 3.71 (s, 3H), 3.69 (s, 2H).

Step B. Methyl 2-fluoro-2-(4-trifluoromethylphenyl)acetate

A 1.0M solution of lithium bis(trimethylsilyl)amide in THF (1.97 mL, 1.97 mmol) was added to a stirred solution of the ester from Step A (391 mg, 1.79 mmol) in THF (4 ml) at −78° C. The yellow solution was stirred at −78° C. for 10 min. A precooled solution of N-fluorobenzenesulfonimide (593 mg, 1.88 mmol) in THF (4 mL) was added dropwise via a cannular. The off-white suspension was allowed to warm slowly to RT over 12 h. Saturated NH$_4$Cl solution was added and the mixture extracted with diethyl ether (3×). The combined organic phase was washed with water (2×), brine, dried (MgSO$_4$) and the solvent removed in vacuo. Flash chromatography (silica, 30% DCM-hexanes) afforded the title compound (270 mg, 64%) as a pale yellow liquid: $^1$H NMR (400 MHz, CDCl$_3$) δ 7.66 (d, J=8.4 Hz, 2H), 7.59 (d, J=8.1 Hz, 2H), 5.85 (d, J=47 Hz, 1H), 3.78 (s, 3H).

Step C. 2-Fluoro-2-(4-trifluoromethylphenyl)acetic acid

A solution of the ester from Step B (270 mg, 1.15 mmol) in methanol (10 mL) containing 5N NaOH solution (1 mL) was stirred at RT for 12 h. The volume of methanol was reduced to ~10% in vacuo. 5% Citric acid solution was added and the mixture extracted with ethyl acetate (4×). The combined organic phase was washed with water (2×), brine, dried (MgSO$_4$) and the solvent removed in vacuo to leave the title compound (266 mg, 100%) as an off-white solid: $^1$H NMR (300 MHz, CD$_3$OD) δ 7.73 (d, J=8.5 Hz, 2H), 7.68 (d, J=8.3 Hz, 2H), 5.99 (d, J=48 Hz, 1H).

Step D. (R)-N-[4-[2-[[2-Hydroxy-2-(pyridin-3-yl)ethyl] amino]ethyl]phenyl]-4-[5-[1-fluoro-1-(4-trifluoromethylphenyl)methyl]-1,2,4-oxadiazol-3-yl]benzenesulfonamide The title compound was prepared as described above for Example 3 using the acid from Step C: $^1$H NMR (400 MHz, CD$_3$OD) δ 8.51 (d, J=2.1 Hz, 1H), 8.42 (dd, J=4.9, 1.6 Hz, 1H), 8.14 (d, J=8.7 Hz, 2H), 7.84 (d, J=8.6 Hz, 2H), 7.81 (m, 1H), 7.79 (s, 4H), 7.38 (dd, J=7.9, 4.9 Hz, 1H), 7.08 (d, J=8.5 Hz, 2H), 7.02 (d, J=8.6 Hz, 2H), 4.79 (m, 1H), 2.95–2.70 (m, 6H).

EXAMPLE 111

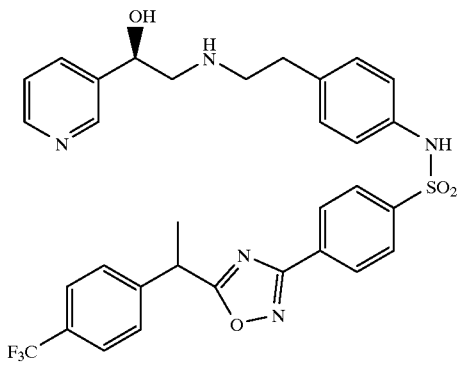

(R)-N-[4-[2-[[2-Hydroxy-2-(pyridin-3-yl)ethyl]amino]ethyl]phenyl]-4-[5-[1-(4-trifluoromethylphenyl)-1-ethyl]-1,2,4-oxadiazol-3-yl]benzenesulfonamide Step A. Methyl 2-methyl-2-(4-trifluoromethylphenyl) acetate A 1.0M solution of lithium bis(trimethylsilyl)amide in THF (2.02 mL, 2.02 mmol) was added to a stirred solution of the ester from Example 110, Step A (400 mg, 1.83 mmol) in THF (8 ml) at −78° C. The solution was stirred at −78° C. for 10 min. Methyl iodide (120 µL, 1.93 mmol) was added. The solution was allowed to warm slowly to RT over 12 h. Saturated NH$_4$Cl solution was added and the mixture extracted with diethyl ether (3×). The combined organic phase was washed with water (2×), brine, dried (MgSO$_4$) and the solvent removed in vacuo. Flash chromatography (silica, 2–3% ethyl acetate-hexanes) afforded the title compound (234 mg, 55%) as a colorless liquid: $^1$H NMR (400 MHz, CDCl$_3$) δ 7.56 (d, J=8.1 Hz, 2H), 7.40 (d, J=8.3 Hz, 2H), 3.77 (q, J=7.1 Hz, 1H), 3.66 (s, 3H), 1.50 (d, J=7.1 Hz, 3H).

Step B. 2-Methyl-2-(4-trifluoromethylphenyl)acetic acid

A solution of the ester from Step A (234 mg, 1.01 mmol) in methanol (10 mL) containing 5N NaOH solution (1 mL) was stirred at RT for 12 h. The volume of methanol was reduced to ~10% in vacuo. 5% Citric acid solution was added and the mixture extracted with ethyl acetate (3×). The combined organic phase was washed with water (2×), brine, dried (MgSO4) and the solvent removed in vacuo to leave the title compound (213 mg, 97%) as an off-white solid: $^1$H NMR (300 MHz, CD$_3$OD) δ 7.60 (d, J=8.5 Hz, 2H), 7.45 (d, J=8.2 Hz, 2H), 3.82 (q, J=7.1 Hz, 1H), 1.55 (d, J=7.2 Hz, 3H).

Step C. (R)-N-[4-[2-[[2-Hydroxy-2-(pyridin-3-yl)ethyl] amino]ethyl]phenyl]-4-[5-[1-(4-trifluoromethylphenyl)-1-ethyl]-[1,2,4]-oxadiazol-3-yl]benzenesulfonamide The title compound was prepared as described above for Example 3 using the acid from Example Step B: $^1$H NMR (400 MHz, CD$_3$OD) δ8.51 (d, J=2.1 Hz, 1H), 8.42 (dd, J=4.9, 1.6 Hz, 1H), 8.14 (d, J=8.5 Hz, 2H), 7.84 (d, J=8.6 Hz, 2H), 7.81 (m, 1H), 7.65 (d, J=8.4 Hz, 2H), 7.55 (d, J=8.3 Hz, 2H), 7.37 (dd, J=7.9, 5.0 Hz, 1H), 7.08 (d, J=8.4 Hz, 2H), 7.02 (d, J=8.6 Hz, 2H), 4.79 (dd, J=7.6, 5.2 Hz, 1H), 4.66 (q, J=7.1 Hz, 1H), 2.91–2.68 (m, 6H), 1.79 (d, J=7.2 Hz, 3H).

Following the procedures outlined for Examples 1–10, 77, and 110–111, the compounds listed in Table 4 were prepared.

TABLE 4

| Example | R | Selected $^1$H NMR Data (CD$_3$OD) |
|---|---|---|
| 112 | 1-(4-fluorophenoxy)-1-methylethyl | 6.93(t, J=8.7Hz, 2H), 6.76(m, 2H), 1.81(s, 6H) |
| 113 | 1-(1-naphthyloxy)-1-methylethyl | 8.2(m, 1H), 7.81–7.78(m, 2H), 7.51–7.45(m, 3H), 7.20(t, J=7.9Hz, 1H), 6.53(d, J=7.1Hz, 1H), 1.95(s, 6H) |
| 114 | 1-(2-naphthyloxy)-1-methylethyl | 7.74(br d, 1H), 7.70(d, J=8.8Hz, 1H), 7.58(br d, 1H), 7.39–7.31(m, 3H), 7.10–7.07(m, 3H), 6.96(dd, J=9.0, 2.4Hz, 1H), 1.89(s, 6H) |
| 115 | 1-(4-chlorophenoxy)-1-methylethyl | 7.19(d, J=8.9Hz, 2H), 6.73(d, J=8.9Hz, 2H), 1.82(s, 6H) |

TABLE 4-continued

[Structure with OH, pyridine, NH, phenyl, SO2, oxadiazole, R group]

| Example | R | Selected $^1$H NMR Data (CD$_3$OD) |
|---|---|---|
| 116 | 1-(2-chlorophenoxy)-1-methylethyl | 7.39–7.36(m, 2H), 7.13–7.02(m, 6H), 6.70(dd, J=8.2, 1.4Hz, 1H), 1.87(s, 6H) |
| 117 | 1,1-difluoro-1-(phenyl)methyl | 7.68(d, J=7.2Hz, 2H), 7.61–7.52 (m, 3H) |
| 118 | 1-(4-(4-chlorophenyl)phenoxy)-1-methylethyl | 7.48(d, J=8.9Hz, 2H), 7.44(d, J=8.6Hz, 2H), 7.38–7.34(m, 3H), 6.81(d, J=8.9Hz, 2H), 1.86(m, 6H) |
| 119 | 1-(4-chlorophenyl)-1-methylethyl, bistrifluoroacetate salt | 7.33(s, 4H), 1.86(s, 6H) |
| 120 | 1-(4-trifluoromethoxyphenyl)-1-ethyl | 7.46(d, 2H), 7.25(d, 2H), 4.60(q, J=7.2Hz, 1H), 1.77(d, J=7.2Hz, 3H) |
| 121 | 1-fluoro-1-(4-trifluoromethoxyphenyl)methyl | 7.69(d, J=7.6Hz, 2H), 7.40–7.36(m, 3H), 6.98(d, J=45Hz, 1H) |
| 122 | 1-(6-fluoronaphth-2-yl)-1-hydroxymethyl | 8.03(br s, 1H), 7.93(dd, J=9.1, 5.7Hz, 1H), 7.86(d, J=8.6Hz, 1H), 7.66(br d, J=8.7Hz, 1H), 7.52(dd, J=10, 2.6Hz, 1H), 7.32(dt, 1H), 6.26(s, 1H) |
| 123 | 1-(6-fluoronaphth-2-yl)-1-ethyl, bistrifluoroacetate salt | 7.90–7.82(m, 5H), 7.53–7.48(m, 2H), 7.30(dt, 1H), 4.72(q, J=7.2Hz, 1H), 1.86(d, J=7.2Hz, 3H) |
| 124 | 1-(6-fluoronaphth-2-yl)-1-methylethyl, bistrifluoroacetate salt | 7.93–7.79(m, 6H), 7.50–7.47(m, 2H), 7.30(dt, 1H), 2.0(s, 6H) |

Following the procedures outlined for Examples 66–71, the compounds listed in Table 5 were prepared.

TABLE 5

[Structure with OH, pyridine, NH, phenyl, SO2, oxadiazole, R group]

| Example | R | Selected $^1$H NMR Data (CD$_3$OD) |
|---|---|---|
| 125 | 4-trifluoromethylphenyl, trifluoroacetate salt | 8.34–8.31(m, 4H), 7.89–7.86(m, 3) |

TABLE 5-continued

| Example | R | Selected $^1$H NMR Data (CD$_3$OD) |
|---|---|---|
| 126 | 4-trifluoromethoxyphenyl, trifluoroacetate salt | 8.25(d, J=9.0Hz, 2H), 7.49–7.46(m, 3H) |

What is claimed is:

1. A compound having the formula:

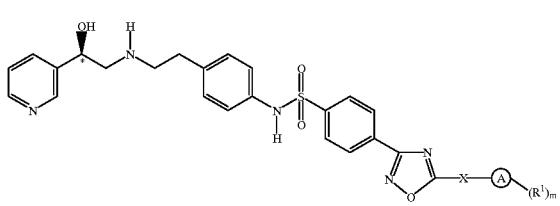

wherein

X is CH$_2$ or CH$_2$O with the carbon being attached to the oxadiazole ring;

m is 1,2 or 3;

A is phenyl; and

R$^1$ is fluoro or trifluoromethoxy; or a pharmaceutically acceptable salt thereof.

2. A compound of claim 1 selected from the group consisting of:

N-[4-[2-[[2-hydroxy-2-(3-pyridinyl)ethyl]amino]ethyl]phenyl]-4-[5-(4-fluorophenylmethyl)-[1,2,4]-oxadiazol-3-yl]benzensulfonamide;

N-[4-[2-[[2-hydroxy-2-(3-pyridinyl)ethyl]amino]ethyl]phenyl]-4-[5-(3,4-difluorophenylmethyl)-[1,2,4]-oxadiazol-3-yl]benzensulfonamide;

N-[4-[2-[[2-hydroxy-2-(3-pyridinyl)ethyl]amino]ethyl]phenyl]-4-[5-(3,4,5-trifluorophenylmethyl)-[1,2,4]-oxadiazol-3-yl]benzensulfonamide;

N-[4-[2-[[2-hydroxy-2-(3-pyridinyl)ethyl]amino]ethyl]phenyl]-4-[5-(4-fluorophenoxymethyl)-[1,2,4]-oxadiazol-3-yl]benzensulfonamide;

N-[4-[2-[[2-hydroxy-2-(3-pyridinyl)ethyl]amino]ethyl]phenyl]-4-[5-(3,4-difluorophenoxymethyl)-[1,2,4]-oxadiazol-3-yl]benzensulfonamide;

N-[4-[2-[[2-hydroxy-2-(3-pyridinyl)ethyl]amino]ethyl]phenyl]-4-[5-(4-trifluoromethoxyphenoxymethyl)-[1,2,4]-oxadiazol-3-yl]benzensulfonamide; and N-[4-[2-[[2-hydroxy-2-(3-pyridinyl)ethyl]amino]ethyl]phenyl]-4-[5-(4-trifluoromethoxyphenylmethyl)-[1,2,4]-oxadiazol-3-yl]benzensulfonamide.

3. A composition for the treatment of diabetes or obesity or for lowering triglyceride or cholestrol levels or increasing high density lipoprotein levels or for decreasing gut motility or for reducing neurogenic inflammation or for treating depression or for treating gastrointestinal disorders which comprises an inert carrier and an effective amount of a compound of claim 1.

4. A pharmaceutical composition which comprises a compound of claim 1 and a pharmaceutically acceptable carrier.

* * * * *